United States Patent [19]
Prieve et al.

[11] Patent Number: 5,931,857
[45] Date of Patent: Aug. 3, 1999

[54] METHOD AND APPARATUS FOR DIAGNOSIS AND TREATMENT OF ARRHYTHMIAS

[75] Inventors: Kathleen Alice Prieve, Shoreview; William A. P. Graham, Minnetrista; David Karl Lee Peterson, Circle Pines, all of Minn.

[73] Assignee: Medtronic, Inc., Minneapolis, Minn.

[21] Appl. No.: 09/046,976

[22] Filed: Mar. 24, 1998

Related U.S. Application Data

[63] Continuation of application No. 08/764,865, Dec. 13, 1996, Pat. No. 5,755,737.

[51] Int. Cl.$^6$ .................................................... A61N 1/362
[52] U.S. Cl. ................................................. 607/14; 607/32
[58] Field of Search ............................ 607/14, 32, 5, 607/6, 4, 9

[56] References Cited

U.S. PATENT DOCUMENTS

| | | |
|---|---|---|
| 3,952,750 | 4/1976 | Mirowski et al. . |
| 4,210,149 | 7/1980 | Heilman et al. . |
| 4,365,633 | 12/1982 | Loughman et al. . |
| 4,651,740 | 3/1987 | Schroeppel . |
| 5,159,926 | 11/1992 | Ljungstroem . |
| 5,190,034 | 3/1993 | Sholder . |
| 5,332,400 | 7/1994 | Alferness . |
| 5,443,486 | 8/1995 | Hrdlicka et al. . |
| 5,490,862 | 2/1996 | Adams et al. . |
| 5,674,249 | 10/1997 | deCoriolis et al. . |

*Primary Examiner*—Scott M. Getzow
*Attorney, Agent, or Firm*—Reed A. Duthler; Harold R. Patton

[57] ABSTRACT

An implantable anti-arrhythmia device such as a defibrillator or anti-tachycardia pacemaker with an associated patient activator. The arrhythmia detection function is divided between the patient and the implanted device, rather than merely providing patient activation or a patient override. The implantable device is provided with a tachyarrhythmia recognition mechanism, which operates essentially continuously, and which, upon meeting a first set of criteria, will trigger delivery of an anti-arrhythmia therapy such as pacing, cardioversion or defibrillation. The patient is provided with an activator which informs the implanted device that the patient believes that anti-arrhythmia therapy is necessary. In response to receipt of the activation signal, the implanted device defines a time interval thereafter during which a second, less stringent set of arrhythmia detection criteria must be met, in response to which the device will deliver a cardioversion or defibrillation pulse.

23 Claims, 15 Drawing Sheets

| PRIOR R EVENT BEAT CODE: | CURRENT R EVENT BEAT CODE: | | | | | | | | | |
|---|---|---|---|---|---|---|---|---|---|---|
| | 0 | 1 | 2 | 3 | 4 | 5 | 6 | 7 | 8 | 9 |
| 0 | 0 [A] | 18 [Z] | 11 [L] | 18 [Z] | 14 [O] | 14 [O] | 14 [O] | 1 [B] | 17 [M] | 3 [D] |
| 1 | 18 [Z] | 5 [F] | 18 [Z] | 18 [Z] | 14 [O] | 14 [O] | 14 [O] | 18 [Z] | 17 [M] | 14 [O] |
| 2 | 12 [M] | 18 [Z] | 6 [G] | 18 [Z] | 14 [O] | 14 [O] | 14 [O] | 10 [K] | 17 [M] | 14 [O] |
| 3 | 18 [Z] | 18 [Z] | 18 [Z] | 13 [N] | 14 [O] | 14 [O] | 14 [O] | 18 [Z] | 17 [M] | 14 [O] |
| 4 | 15 [P] | 15 [P] | 15 [P] | 15 [P] | 16 [Q] | 16 [Q] | 16 [Q] | 18 [Z] | 17 [M] | 16 [Q] |
| 5 | 15 [P] | 15 [P] | 15 [P] | 15 [P] | 16 [Q] | 16 [Q] | 16 [Q] | 7 [H] | 17 [M] | 16 [Q] |
| 6 | 15 [P] | 9 [J] | 18 [Z] | 18 [Z] | 2 [C] | 8 [I] | 18 [Z] | 18 [Z] | 18 [Z] | 2 [C] |
| 7 | 18 [Z] | 17 [M] | 17 [M] | 17 [M] | 17 [M] | 17 [M] | 17 [M] | 18 [Z] | 17 [M] | 17 [M] |
| 8 | 17 [M] | 15 [P] | 15 [P] | 15 [P] | 16 [Q] | 16 [Q] | 16 [Q] | 18 [Z] | 17 [M] | 16 [Q] |
| 9 | 4 [E] | | | | | | | | | |

FIG. 7

| PATTERN CODE: | CURRENT STATE: | | | | | | | | | |
|---|---|---|---|---|---|---|---|---|---|---|
| | 0 [RESET] | 19 [A] | 38 [B] | 57 [CD] | 76 [E] | 95 [A1] | 114 [A2] | 133 [L] | 152 [M] | 171 [Z] |
| [A] 0 | 19 | 19 | 0 | 0 | 114 | 114 | 19 | 0 | 95 | 95 |
| [B] 1 | 38 | 38 | 0 | 0 | 0 | 0 | 0 | 0 | 0 | 0 |
| [C] 2 | 57 | 0 | 57 | 0 | 0 | 0 | 0 | 0 | 0 | 0 |
| [D] 3 | 57 | 57 | 0 | 0 | 0 | 0 | 0 | 0 | 0 | 0 |
| [E] 4 | 76 | 0 | 0 | 76 | 0 | 0 | 0 | 0 | 0 | 0 |
| [F] 5 | 0 | 0 | 0 | 0 | 0 | 0 | 0 | 0 | 0 | 0 |
| [G] 6 | 0 | 0 | 0 | 0 | 0 | 0 | 0 | 0 | 0 | 0 |
| [H] 7 | 0 | 0 | 0 | 0 | 0 | 0 | 0 | 0 | 0 | 0 |
| [I] 8 | 0 | 0 | 0 | 0 | 0 | 0 | 0 | 0 | 0 | 0 |
| [J] 9 | 0 | 0 | 0 | 0 | 0 | 0 | 0 | 0 | 0 | 0 |
| [K] 10 | 0 | 0 | 0 | 0 | 0 | 0 | 0 | 0 | 0 | 0 |
| [L] 11 | 133 | 133 | 0 | 0 | 0 | 0 | 0 | 0 | 0 | 0 |
| [M] 12 | 152 | 0 | 0 | 0 | 0 | 0 | 0 | 152 | 0 | 0 |
| [N] 13 | 0 | 0 | 0 | 0 | 0 | 0 | 0 | 0 | 0 | 0 |
| [O] 14 | 0 | 0 | 0 | 0 | 0 | 0 | 0 | 0 | 0 | 0 |
| [P] 15 | 0 | 0 | 0 | 0 | 0 | 0 | 0 | 0 | 0 | 0 |
| [Q] 16 | 0 | 0 | 0 | 0 | 0 | 0 | 0 | 0 | 0 | 0 |
| [Y] 17 | 0 | 0 | 0 | 0 | 0 | 0 | 0 | 0 | 0 | 0 |
| [Z] 18 | 171 | 0 | 171 | 0 | 0 | 0 | 0 | 0 | 0 | 0 |

FIG. 8

| VENTRICULAR BEAT CODE | CURRENT STATE | | | | |
|---|---|---|---|---|---|
| | [RESET] [0] | STATE 2 [10] | STATE 0 [20] | STATE 3 [30] | STATE 4 [40] |
| 0 | 20 | 20 | 20 | 10 | 10 |
| 1 | 40 | 0 | 40 | 0 | 0 |
| 2 | 40 | 0 | 40 | 0 | 0 |
| 3 | 0 | 0 | 0 | 0 | 0 |
| 4 | 20 | 20 | 20 | 10 | 10 |
| 5 | 30 | 0 | 30 | 0 | 0 |
| 6 | 30 | 0 | 30 | 0 | 0 |
| 7 | 40 | 0 | 40 | 0 | 0 |
| 8 | 0 | 0 | 0 | 0 | 10 |
| 9 | 20 | 20 | 20 | 10 | 10 |

FIG. 9

| PATTERN CODE | CURRENT STATE | | |
|---|---|---|---|
| | 0 [RESET] | 19 [QY] | 38 [P] |
| 0[A] | 0 | 0 | 0 |
| 1[B] | 0 | 0 | 0 |
| 2[C] | 0 | 0 | 0 |
| 3[D] | 19 | 19 | 19 |
| 4[E] | 19 | 19 | 19 |
| 5[F] | 0 | 0 | 0 |
| 6[G] | 0 | 0 | 0 |
| 7[H] | 0 | 0 | 0 |
| 8[I] | 0 | 0 | 0 |
| 9[J] | 0 | 0 | 0 |
| 10[K] | 0 | 0 | 0 |
| 11[L] | 0 | 0 | 0 |
| 12[M] | 0 | 0 | 0 |
| 13[N] | 0 | 0 | 0 |
| 14[O] | 19 | 0 | 19 |
| 15[P] | 38 | 38 | 0 |
| 16[Q] | 19 | 19 | 19 |
| 17[Y] | 19 | 19 | 19 |
| 18[Z] | 0 | 0 | 0 |

FIG. 10

| PATTERN CODE: | CURRENT STATE: | | | | | | |
|---|---|---|---|---|---|---|---|
| | [RESET] 0 | [FG] 19 | [O] 38 | [H1] 57 | [H2] 76 | [J] 95 | [N] 114 |
| [A] 0 | 0 | 0 | 0 | 0 | 0 | 0 | 0 |
| [B] 1 | 0 | 0 | 0 | 0 | 0 | 0 | 0 |
| [C] 2 | 0 | 0 | 0 | 0 | 0 | 0 | 0 |
| [D] 3 | 0 | 0 | 0 | 0 | 0 | 0 | 0 |
| [E] 4 | 0 | 0 | 0 | 0 | 0 | 0 | 0 |
| [F] 5 | 19 | 19 | 0 | 0 | 0 | 19 | 0 |
| [G] 6 | 19 | 19 | 0 | 0 | 0 | 19 | 0 |
| [H] 7 | 57 | 0 | 57 | 0 | 0 | 0 | 76 |
| [I] 8 | 114 | 0 | 0 | 114 | 0 | 0 | 0 |
| [J] 9 | 95 | 0 | 0 | 95 | 95 | 0 | 0 |
| [K] 10 | 0 | 0 | 0 | 0 | 0 | 0 | 0 |
| [L] 11 | 0 | 0 | 0 | 0 | 0 | 0 | 0 |
| [M] 12 | 0 | 0 | 0 | 0 | 0 | 0 | 0 |
| [N] 13 | 0 | 0 | 0 | 0 | 0 | 0 | 0 |
| [O] 14 | 38 | 38 | 0 | 0 | 0 | 0 | 0 |
| [P] 15 | 0 | 0 | 0 | 0 | 0 | 0 | 0 |
| [Q] 16 | 0 | 0 | 0 | 0 | 0 | 0 | 0 |
| [Y] 17 | 0 | 0 | 0 | 0 | 0 | 0 | 0 |
| [Z] 18 | 0 | 0 | 0 | 0 | 0 | 0 | 0 |

FIG. 11

METHOD AND APPARATUS FOR DIAGNOSIS AND TREATMENT OF ARRHYTHMIAS

This application is a continuation of application Ser. No. 08/764,865, filed 13 Dec. 1996 now U.S. Pat. No. 5,755,737.

BACKGROUND OF THE INVENTION

This invention relates to devices which detect and/or treat tachyarrhythmias (rapid heart rhythms), and more specifically, to mechanisms to distinguish among various tachyarrhythmias and to provide appropriate therapies to treat the identified tachyarrhythmias.

In conjunction with implantable cardioverters and defibrillators, numerous mechanisms for communication between the patient and the implanted device have been proposed. Particularly in conjunction with implantable defibrillators or cardioverters, the provision of a patient warning signal indicating that cardioversion or defibrillation is about to commence, is disclosed in U.S. Pat. No. 4,210,149 issued to Heilman et al, U.S. Pat. No. 5,332,400 issued to Alferness and U.S. Pat. No. 5,190,034 issued to Sholder. The warning signals provided to the patient typically take the form of audio signals or electrical stimulation using electrodes associated with the implanted device.

In addition to communication from the implanted device to the patient, communication and control signals from the patient to the device are also known to the art. For example, U.S. Pat. No. 5,443,486 issued to Hrdlicka et al and U.S. Pat. No. 4,365,633 issued to Loughman et al, both disclose devices allowing the patient to program or control the operation of the implanted device. Particularly in conjunction with implanted defibrillators, the warning and control functions have been integrated, so that the patient is provided with a warning signal prior to defibrillation or cardioversion, and with a mechanism for overriding the implanted device, to prevent delivery of an undesired or unneeded cardioversion or defibrillation pulse. Such systems are disclosed in U.S. Pat. No. 5,190,034 issued to Sholder and U.S. Pat. No. 4,210,149 issued to Heilman et al, cited above. In such systems, the implanted device monitors the patient's heart rhythm to determine the presence of an arrhythmia requiring cardioversion or defibrillation. Having detected such a rhythm, the device provides the warning signal indicating the imminent delivery of a cardioversion or defibrillation shock, which the patient may then override. Allowing the patient to initiate delivery of a cardioversion or defibrillation shock is also known to the art. For example, U.S. Pat. No. 3,952,750 issued to Mirowski et al discloses atrial implantable cardioverter in which the patient initiates delivery of an atrial cardioversion pulse, and U.S. Pat. No. 5,498,062 issued to Adams et al discloses an implantable defibrillator in which the patient initiates operation of the arrhythmia detection mechanism, to determine whether delivery of a cardioversion or defibrillation pulse is necessary.

Presently available implantable anti-arrhythmia devices employ sophisticated arrhythmia detection and classification methods to accurately determine whether delivery of therapy is appropriate. Particularly in the context of devices such as cardioverters and defibrillators which have the potential to induce arrhythmias if not appropriately synchronized to the patient's heart rhythm, these detection methods tend to be conservative, in order to avoid delivery of unnecessary therapy. In such cases, it may sometimes take the implanted device longer than the patient to determine that delivery of a therapy is needed. Patient activators as discussed above which trigger therapy on request address this problem, but do not provide for the possibility of patient error. The device described in the Adams patent cited above deals with the possibility of patient error by determining whether therapy is appropriate after a request by the patient, but employs the same set of criteria for patient requested therapy as for device initiated therapy, and thus may not provide for therapies as quickly or as often as may be desirable in response to patient's requests. The present invention is believed to offer the patient the ability to quickly and safely receive therapy in response to a request, when appropriate.

SUMMARY OF THE INVENTION

The present invention is directed toward an implantable anti-arrhythmia device such as a defibrillator or anti-tachycardia pacemaker with an associated patient activator. The arrhythmia detection function is divided between the patient and the implanted device, rather than merely providing patient activation or a patient override. In the present invention, the implantable device is provided with a tachyarrhythmia recognition mechanism, which operates essentially continuously, and which, upon meeting a first set of criteria, will trigger delivery of an anti-arrhythmia therapy such as pacing, cardioversion or defibrillation. In addition, the patient is provided with an activator which informs the implanted device that the patient believes that anti-arrhythmia therapy is necessary. In response to receipt of the activation signal, the implanted device defines a time interval thereafter during which a second, less stringent set of arrhythmia detection criteria must be met, in response to which the device will deliver a cardioversion or defibrillation pulse. By this mechanism, more stringent criteria are defined for self-activation of the device than for patient activation, which is believed to enhance the accuracy and flexibility of the system in dealing with tachyarrhythmias as compared to the systems described above.

In a preferred embodiment of the invention, the particular therapy to be initiated is programmed into the implanted device, and takes priority over automatic, device-initiated therapies. In the preferred embodiment disclosed herein, the patient-activated therapy is directed towards termination of atrial tachyarrhythmias. However, the invention generally is believed applicable in the context of detection and termination of ventricular arrhythmias as well. In the particular embodiment disclosed herein, an atrial anti-arrhythmia therapy is delivered in response to the patient's request for therapy only if the heart's rhythm meets criteria consistent with atrial fibrillation or atrial tachycardia, within a predetermined time interval, e.g., one minute, after the patient-activated therapy was requested. In addition, the patient-activated therapy is disabled on occurrence of a variety of events, including detection of termination of the atrial fibrillation or atrial tachycardia episode or a determination that sustained atrial fibrillation or tachycardia has persisted for more than a pre-determined period. In response to the patient activation signal, the implanted device notifies the activator whether an atrial rhythm appropriate for treatment is present and whether a therapy is available for delivery in response to the patient's request.

BRIEF DESCRIPTION OF THE DRAWINGS

FIG. 7 is a table illustrating the operation of a continuous recognition machine employed by a preferred embodiment of the present invention to accomplish classification of heart event sequences according to the system illustrated in FIG. 4.

FIG. 8 is a table illustrating the operation of a continuous recognition machine employed by a preferred embodiment of the present invention to identify the probable occurrence of normal sinus rhythm or sinus tachycardia based upon series of heart event sequences as classified using the continuous recognition machine illustrated in FIG. 5.

FIG. 9 is a table illustrating the operation of a continuous recognition machine employed by a preferred embodiment of the present invention to identify the probable occurrence of normal sinus rhythm or sinus tachycardia in the presence of far field R-wave sensing in the atrium, based upon series of heart event sequences as classified using the continuous recognition machine illustrated in FIG. 5.

FIG. 10 is a table illustrating the operation of a second continuous recognition machine employed by a preferred embodiment of the present invention to identify the probable occurrence of atrial fibrillation or flutter based upon series of heart event sequences as classified using the continuous recognition machine illustrated in FIG. 5.

FIG. 11 is a table illustrating the operation of a continuous recognition machine employed by a preferred embodiment of the present invention to identify the probable occurrence of AV nodal tachycardia based upon series of heart event sequences as classified using the continuous recognition machine illustrated in FIG. 5.

DETAILED DESCRIPTION OF THE PREFERRED EMBODIMENTS

Figure 1:
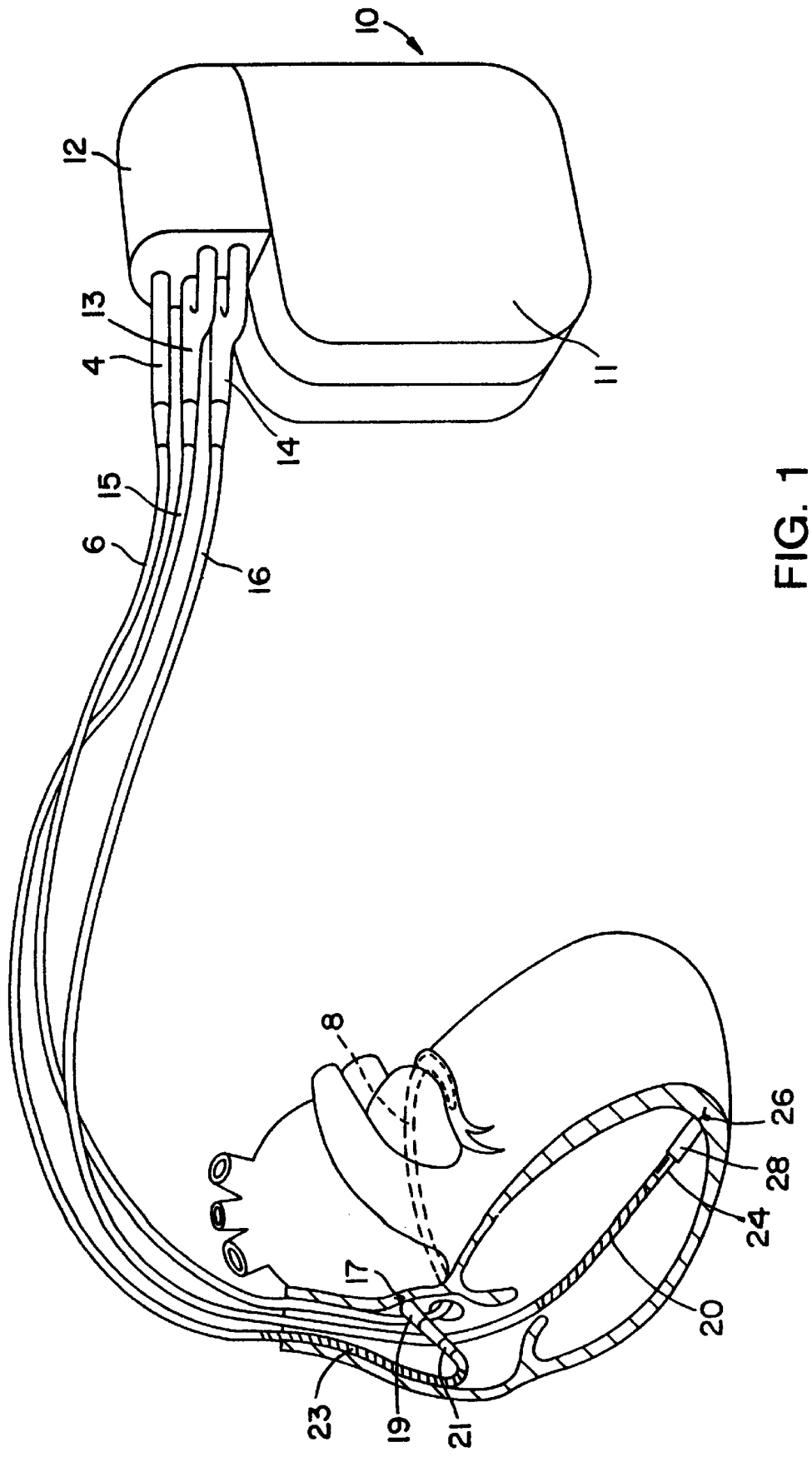
FIG. 1 illustrates a first embodiment of an implantable pacemaker/cardioverter/defibrillator of a type appropriate for use in practicing the present invention, in conjunction with a human heart.

FIG. 1 illustrates a defibrillator and lead set according to the present invention. The ventricular lead includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coil electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding to the structure of the ventricular lead. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably is 10 cm in length or greater and is configured to extend from the SVC toward the tricuspid valve. In one preferred embodiment tested by the inventors, approximately 5 cm of the right atrium/SVC electrode was located in the right atrium, with the remaining 5 cm located in the SVC. At the proximal end of the lead is a bifurcated connector 13 which carries three electrical connectors, each coupled to one of the coiled conductors.

The coronary sinus lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may op course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
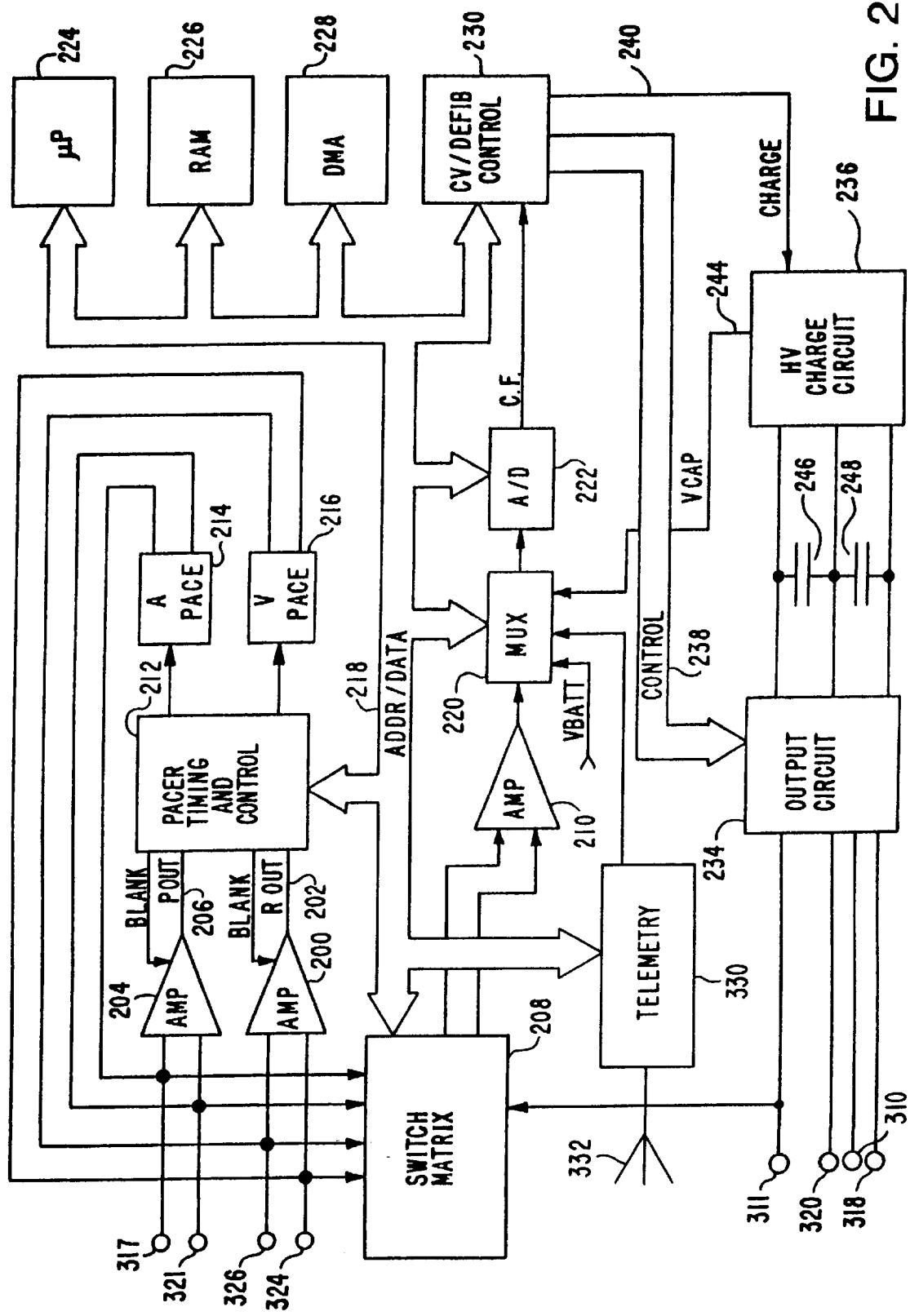
FIG. 2 illustrates a functional schematic diagram of an implantable pacemaker/cardioverter/defibrillator in which the invention may be practiced.

FIG. 2 is a functional schematic diagram of an implantable pacemaker/cardioverter/ defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on Rout line 202 whenever the signal sensed between electrodes 324 and 326 exceeds the present sensing threshold.

Electrodes 317 and 321 are coupled to the P-wave amplifier 204. which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued June 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be per-formed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 (FIG. 2) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, as discussed in the Background of the Invention section above might also usefully be employed in alternative embodiments of the invention.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties. In addition, high frequency pulse bursts may be delivered to electrodes 317 and 321 to terminate atrial tachyarrhythmias, as described in PCT Patent Publication No. WO95/28987, filed by Duffin et al and PCT Patent Publication No. WO95/28988, filed by Mehra et al, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, high frequency burst stimulation as discussed above may be employed as the initial attempted therapy. Subsequent therapies may be delivery of high amplitude defibrillation pulses, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
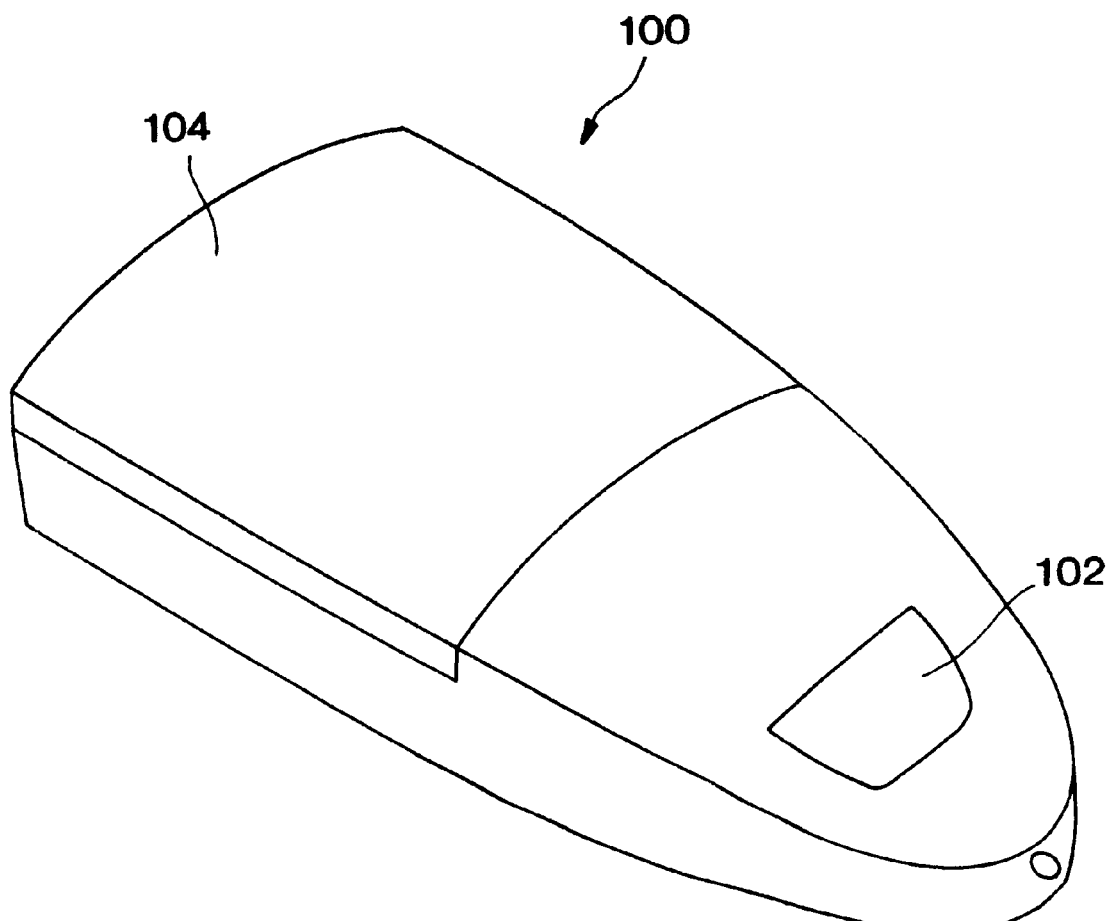
FIG. 3 illustrates an exemplary embodiment of a patient activator which may be used in practicing the present invention.

FIG. 3 illustrates the general physical configuration of a patient activator of the type which may be employed with the present invention. The activator 100 generally takes the form of a plastic enclosure provided with a push button 102 by which the patient may request delivery of the predefined patient-initiated therapy. The device is battery powered, employing batteries accessible by means of the battery cover 104. On the reverse side of the device, not visible, are two indicator lights, one green, one amber, which are used to provide information to the patient with regard to the status and functioning of the patient-initiated therapy.

Figure 4:
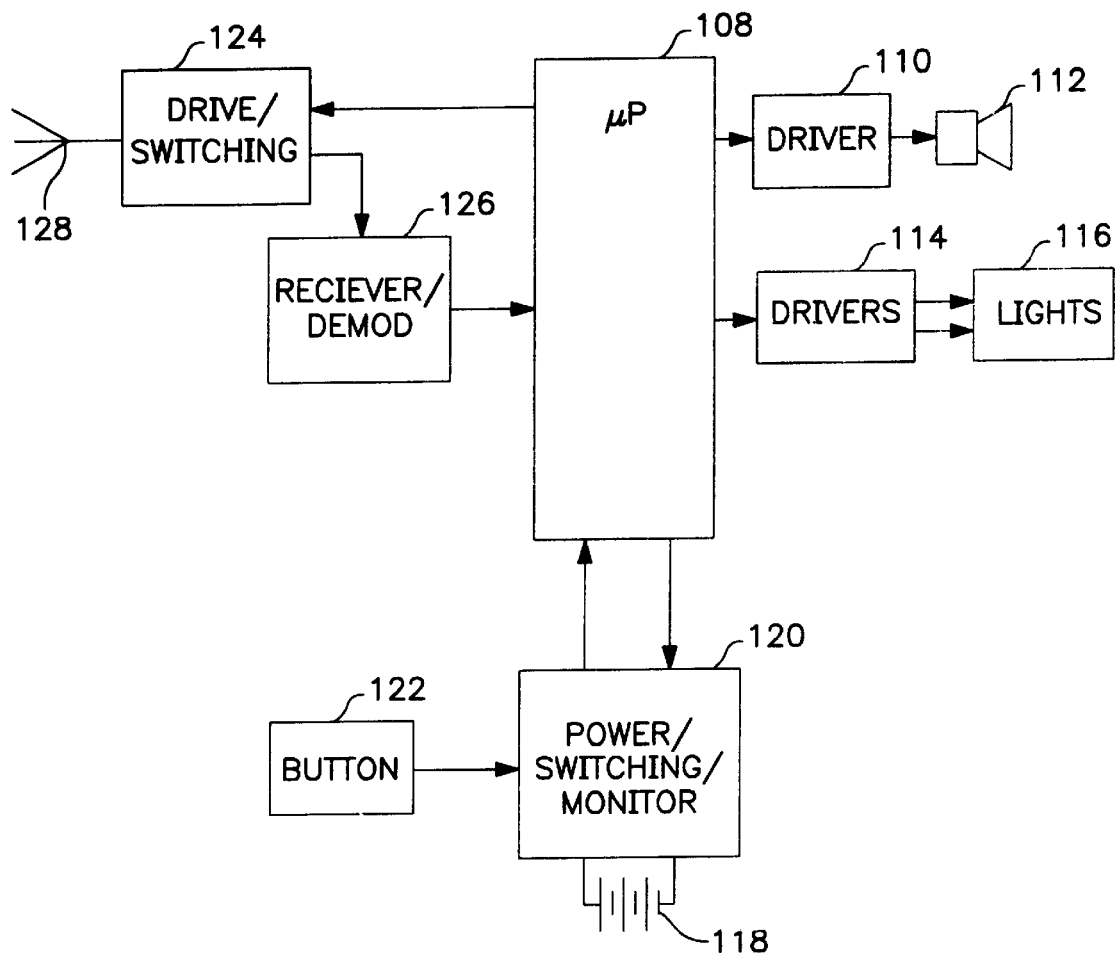
FIG. 4 is a functional block diagram of the patient activator of FIG. 3.

FIG. 4 is a block functional diagram of a patient activator of the type appropriate for use in conjunction with the present invention. This device corresponds generally to patient activators presently available commercially for use in conjunction with implanted Medtronic pacemakers, and in particular, corresponds generally to the Medtronic Model-9462 patient activator presently in commercial distribution for use in conjunction with implanted bradycardia pacers. Control functions are provided by microprocessor 108, based upon programming stored in its associated read-only memory located therein. Microprocessor 108 provides output signals for producing audible patient alert signals by means of driver 110 and speaker 112. Microprocessor 108 also provides control signals to LED driver 114 to power the associated amber and green colored LEDs 116, referred to above. The device is powered by a battery 118 which is coupled to the microprocessor 108 by means of power/switching/battery monitor circuitry 120, which also provides the microprocessor with an indication that push button 122 has been pressed.

Communication with microprocessor 108 is accomplished by means of the antenna driver/switching circuit 124, the receiver demodulator 126 and RF antenna 128. Transmissions from the implanted device are received by antenna 128, and are demodulated by receiver demodulator 126 to be provided to the microprocessor. In response to received transmissions from the implanted device, the microprocessor controls operation of the audio and light drivers 110 and 114 to indicate the nature of the communication received. Transmissions to the implanted device, for example, in response to activation of the push button 102 are provided by microprocessor 108 to the antenna drive/switching circuit, which then communicates with the implanted device by means of antenna 128.

1. Arrhythmia Detection for Device Initiated Therapy

The implanted device employs a sophisticated arrhythmia detection and classification methodology to initiate delivery of anti-arrhythmia therapy. However, in some circumstances the patient may be aware of the presence of tachyarrhythmia before the implanted device has confirmed its presence, and may employ the activator to request delivery of an anti-arrhythmia therapy. In such case, the implanted device employs a less stringent set of criteria to determine whether therapy is appropriate, and communicates its status to the patient by means of the lights and tones provided by the activator.

The arrhythmia detection and classification system normally employed by the implanted device according to the present invention to trigger delivery of anti-arrhythmia therapy may be any of the numerous arrhythmia detection methodologies employed to trigger delivery of anti-arrhythmia therapy in the patents cited herein. In the preferred embodiment of the present invention disclosed herein, the implanted device employs a prioritized set of inter-related rules for arrhythmia detection. Each rule contains a set of one or more "clauses" which must be satisfied (criteria which must be met). While all clauses of a rule are satisfied, the rule is indicated to be met. In the context of the present application this is referred to as the rule "firing". It is possible for multiple rules to be "firing" at the same time, with the highest priority rule taking precedence. Some rules trigger, delivery of therapy when firing. Other rules inhibit delivery of therapy when firing. The highest priority rule firing at any specific time controls the behavior of the device. For example, the firing of a rule which triggers therapy is superseded by the firing of higher priority rules preventing delivery of therapy. Rules cease firing when their clauses cease to be satisfied, whether or not a therapy is triggered by the rule.

Each rule includes a set of clauses or criteria which, when satisfied, indicate the likely occurrence of a specified type of heart rhythm, including various tachyarrhythmias, sinus tachycardia and normal sinus rhythm. A specific rhythm or tachyarrhythmia may have more than one associated rule. The rules are interrelated, such that progress toward meeting the requirements of a clause of one rule may also be the subject matter of a clause of a different rule.

The specific criteria set forth by the clauses of the various rules as disclosed include a number of known criteria for evaluating heart rhythm, including the entire arrhythmia detection and classification system employed in the presently available Medtronic 7219 pacemaker cardioverter defibrillators, as well as criteria disclosed in U.S. Pat. No. 5,330,508, issued to Gunderson, as will be discussed below. In addition, a number of new evaluation criteria are included within the clauses of various rules. One such new detection methodology is based upon the classification of the events occurring associated with the sequence of two ventricular depolarizations into a limited number of event patterns, based upon the number and times of occurrences of atrial events, preceding the two most recent ventricular events. An event pattern is developed for each individual ventricular event, so that successive event patterns overlap one another. The inventors have determined that certain sequences of event patterns are strongly indicative of specific types of heart rhythms. For heart rhythms of which this is true, a defined set of indicative event pattern sequences or a "grammar" is defined. Adherence of the heart rhythm to the grammars associated with various heart rhythms is determined by simultaneously operating continuous recognition machines, the outputs of which form the subject matter of one or more clauses, within the hierarchy of rules.

In a preferred embodiment of the invention, the device is provided with rules which when satisfied indicate the presence of sustained atrial fibrillation and sustained atrial flutter and in response to detection thereof delivers anti-atrial fibrillation or anti-atrial tachycardia therapies. These rules include a set of various new classification criteria, including an atrial fibrillation/ atrial tachycardia evidence counter which is incremented and decremented on a beat by beat basis and compared with a defined threshold count or counts taken as indicative of atrial fibrillation or atrial tachycardia. The atrial rate and regularity is also monitored and atrial fibrillation or atrial tachycardia is preliminarily detected when the evidence counter is at or above such a threshold and the atrial rhythm meets defined rate zone criteria associated with atrial fibrillation or atrial tachycardia. When both the evidence count and the rate zone criteria are met, the arrhythmia underway is preliminarily determined to be atrial fibrillation or atrial tachycardia, depending on which rate zone criteria are met. A sustained atrial fibrillation/atrial tachycardia duration timer is then initiated and continues to time until termination of atrial tachyarrhythmia is detected. The time duration since the preliminary detection of an atrial tachyarrhythmia is continually compared to one or more minimum duration values associated with the atrial tachyarrhythmia determined to presently be underway and/or the next scheduled therapy for such arrhythmia. If the time duration since preliminary detection of atrial arrhythmia meets or exceeds the applicable minimum duration value, and other associated criteria are also met, the next scheduled anti-atrial arrhythmia therapy is delivered.

Additional associated criteria which must be met as a prerequisite to delivery of atrial anti-tachyarrhythmia therapies may include expiration of a minimum interval from the most recently delivered therapy not followed by a detected termination of atrial tachyarrhythmia, confirmation that the most recent heart cycles do not indicate a return to sinus rhythm, time duration since preliminary detection of atrial tachyarrhythmia being less than a maximum duration value, time of day corresponding to a predefined time range and/or less than a preset number of atrial anti-arrhythmia therapies having been delivered in a preceding time period.

Figure 5:
FIG. 5 illustrates the basic timing intervals employed by a preferred embodiment of the present invention to classify sequences of heart events.

With each ventricular event, the timing of atrial and ventricular events occurring during the preceding two R-R intervals is analyzed to develop a "pattern code". FIG. 5 illustrates the various defined time intervals, employed to develop the pattern codes. Each of the two R-R intervals is divided into four zones, in which zone 1 encompasses the first 50 milliseconds following the ventricular event initiating the R-R interval, zone 2 extends from the end of zone 1 until halfway through the R-R interval. Zone 3 extends from halfway through the R-R interval to 80 milliseconds prior to the ventricular event ending the R-R interval and zone 4 includes the last 80 milliseconds of the R-R interval.

In order to determine the pattern codes, each individual R-R interval is assigned a "beat code", based on the number of occurrence of atrial events during the R-R interval, and their location with regard to the four defined zones. Three criteria are evaluated in order to assign each R-R interval with a beat code, including the number of atrial events occurring during the R-R interval, referred to as the "P count", the duration of the R-P interval associated with the R-R interval, and the duration of the P-R interval associated with the R-R interval. The R-P interval is the time in milliseconds from the beginning ventricular event in the RR interval to the first atrial event occurring within the interval, if any. The P-R interval is the time in milliseconds from the last atrial event in the R-R interval, if any, to the concluding ventricular event in the R-R interval. It should be noted that if multiple atrial events occur during the R-R interval, the sum of the R-P and P-R intervals will not equal the R-R interval. Based on the P count and the times of occurrence of the atrial depolarizations, a beat count of zero to nine is generated. The algorithm for generating the beat code is as follows.

If P count equals 1 and an atrial event occurs in zone 3, the beat code is zero. If P count equals 1 and the atrial event occurs in zone 1, the beat code is 1. If P count equals 1 and the atrial event occurs in zone 4, the beat code is 2. If P count equals 1 and the atrial event occurs in zone 2, the beat code is 3.

If P count equals 2, and an atrial event occurs in zone 3 but not zone 1, the beat code is 9. If P count equals 2 and an atrial event occurs in zone 3 and in zone 1, the beat code is 4. If P count equals 2 and atrial events occur in zones 1 and 4, the beat code is 5. All other R-R intervals containing two atrial events result in a beat code of 6.

If P count is greater than or equal to 3, the beat code is 8. If P count is equal to 0, the beat code is 7.

Figure 6:
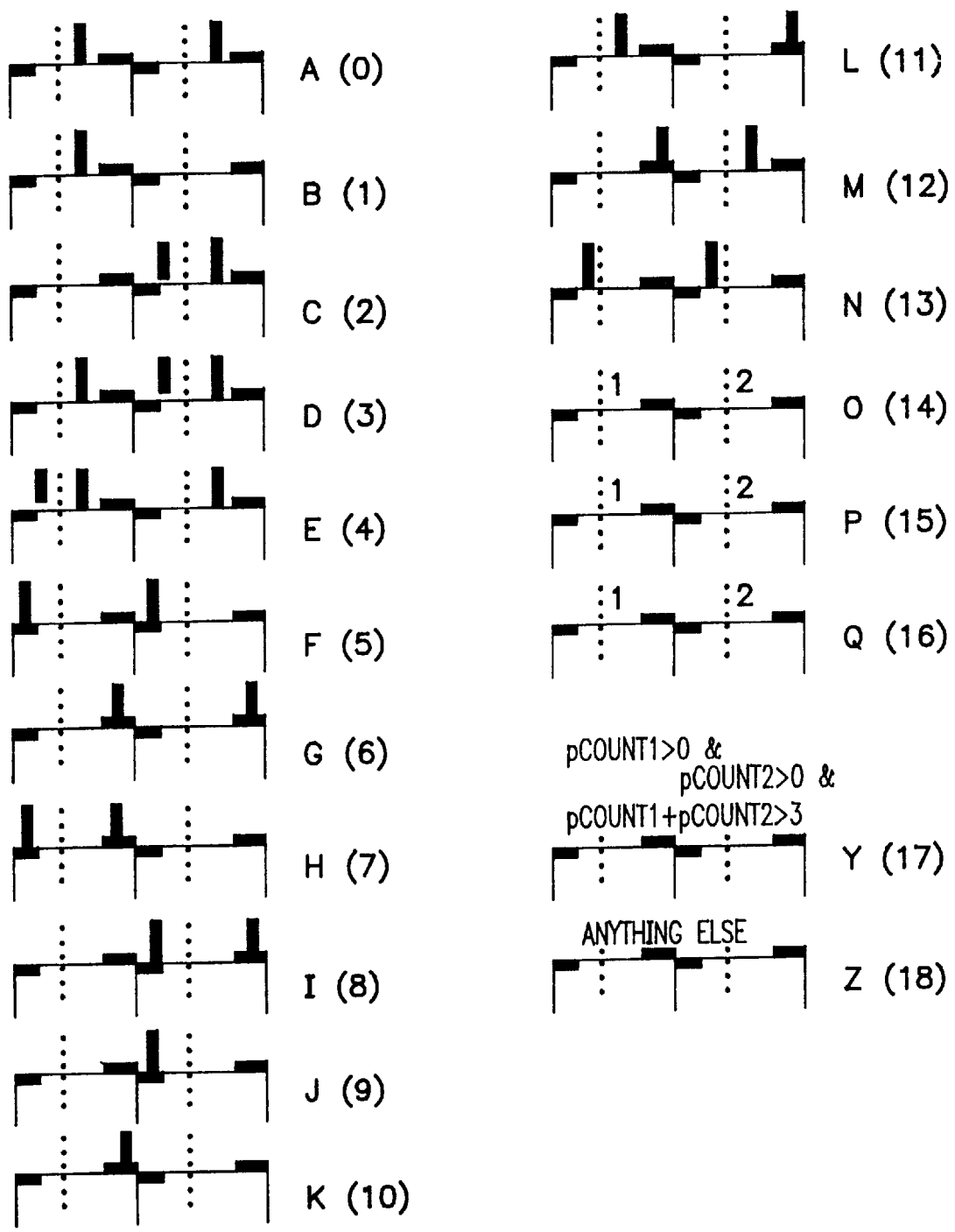
FIG. 6 illustrates the classification system employed by a preferred embodiment of the present invention to classify sequences of heart events.

Given 10 beat codes, it would be expected that 100 corresponding pattern codes for two R-R interval sequences would be generated. However, the inventors have determined that the library of event patterns may usefully be reduced substantially, and have derived a set of 18 pattern codes as illustrated in FIG. 6. In the illustrations, two successive R-R intervals are illustrated, with downward extending lines indicative of ventricular events and upward extending lines indicative of atrial events. Zone 1 is illustrated as a short horizontal bar extending from the first ventricular event in each R-R interval. Zone 4 is illustrated as a short horizontal bar extending back from the last ventricular event in each R-R interval. A vertically extending dotted line is indicative of the dividing line between zone 2 and zone 3, halfway through the R-R interval, upwardly extending lines, coupled to the horizontal base line are indicative of atrial events occurring in the specific zone illustrated. Upwardly extending lines which float above the base line are indicative of atrial events that may occur in either of the two zones to which they are adjacent.

Pattern code A, corresponding to a beat code pair (0,0) is a pattern code sinus tachycardia.

Pattern code B, corresponding to beat code (0,7) arises, among other times, when a premature ventricular contraction occurs and is detected prior to the next atrial depolarization.

Pattern code C corresponds to beat code pairs (7,4) or (7,9), and arises, among other times, in the aftermath of isolated PVC'S.

Pattern code D, corresponding to beat code pairs (0,4) or (0,9) arises, among other times, when an isolated premature atrial contraction occurs, with no corresponding ventricular event.

Pattern code E, corresponding to beat code pairs (4,0) or (9,0) arises, among other times, in the aftermath of an isolated PAC, with resumption of normal sinus rhythm.

Pattern code F, corresponding to beat code pair (1,1) arises, among other times, during a junctional rhythm, with the atrial depolarizations being detected closely following depolarizations in the ventricles. It also arises in disassociated rhythms in which the atria and ventricles beat independently, but slightly out of phase.

Pattern code G, corresponding to beat code pair (2,2) arises, among other times, when a rhythm has a junctional origin, with ventricular depolarizations detected just slightly after atrial depolarizations. It also arises in disassociated rhythms in which atria and ventricle beat independently at close to the same rate, but slightly out of phase.

Pattern code H, corresponding to beat code pair (5,7) arises, among other times, in junctional rhythms in which atrial and ventricular depolarizations are sensed closely spaced to one another, but in no consistent time order.

Pattern code 1, corresponding to beat code pair (7,5) and pattern code J, corresponding to beat code pair (7,1) are both employed for recognition of AV nodal reentrant tachycardia.

Pattern code K, corresponding to beat code pair (2,7) arises, among other times during nodal rhythms, as well as ventricular tachycardia, ventricular fibrillation and ventricular flutter, but rarely, if at all, occurs in cases of atrial fibrillation.

Pattern code L, corresponding to beat code (0,2) occasionally arises in cases of dual tachycardia, in which the atria and ventricles are beating independently, but out of phase.

Pattern code M, beat code pair (2,0) also arises in these situations.

Pattern code N, corresponding to beat code pair (3,3) arises in cases of ventricular tachycardia with one to one retrograde conduction.

Pattern code O is a default pattern code, based on the failure of the pattern code to correspond to any of codes A-N, above, with the additional requirement that the P count for the first R-R interval is 1 and the P count for the second R-R interval is 2. This pattern code arises frequently in atrial fibrillation, among other rapid atrial rhythms. Pattern code P is also a default pattern code, designated if the beat code pair does not correspond to any of the beat code pairs designated in conjunction with pattern codes A-N, above, with a P count for the first R-R interval of 2 and a P count for the second R-R interval of 1.

Pattern code Q is a default pattern code assigned in response to beat code pairs which do not correspond to any of pattern codes A-N above, in which both P counts are 2. Like pattern codes O and P, this pattern code is indicative of atrial fibrillation, and/or rapid atrial rhythms.

Pattern Code Y is a default pattern code assigned to all beat code pairs not falling into any of previously defined pattern codes A-Q, in which there is at least one atrial event in each R-R interval, and the sum of the two P counts exceeds 3. Pattern code Z is a default pattern code assigned to all beat code pairs not corresponding to any of pattern codes A-Y above.

While the above rules appear to be complex, they may be very conveniently implemented by means of a look up table, as set forth in FIG. 7, which assigns each of the 100 possible beat code pairs to one of the designated pattern codes. By use of the look up table stored in memory, the microprocessor within the device can readily and rapidly determine the appropriate pattern code associated with each successive ventricular event. These pattern codes can be stored as numbers, as indicated in parentheses in FIG. 6, and their order analyzed by means of a software implemented continuous recognition machine to determine whether the sequences of pattern codes correspond to defined grammars corresponding to specific arrhythmias or groups of arrhythmias. The operation of the continuous recognition machines in order to accomplish this result is discussed in more detail, below. However, for purposes of understanding the general operation of the device, in conjunction with the functional flowcharts of FIG. 13, it need only be understood that the continuous recognition machines output a count indicative of the degree of correspondence of the sensed rhythm to the defined grammars for each arrhythmia, and that the rules for identifying the various arrhythmias include clauses setting forth criteria against which the output counts of the continuous recognition machines are compared.

Several of the rules employ continuous recognition machines implemented by the microprocessor, which applies sequences of pattern codes or beat codes, as they are generated with each ventricular event, to an associated look-up table. Each look up table defines a set of sequential states, indicated by bracketed numbers, beginning with the reset state [0], and a set of other defined states, arranged horizontally across the table. Possible pattern codes or beat codes are listed vertically. In operation, with each ventricular event, the processor determines its present state and the most recent pattern or beat code. Based on the table, the processor transitions to the next state, and awaits the next pattern or beat code. As long as the pattern or beat codes adhere to the defined grammar for the rhythm in question, the reset state is avoided. Adherence to the defined grammar over an extended sequence of beats is determined by means of a corresponding count, which may be incremented with each pattern or beat code adhering to the grammar, and may be reset to zero or decremented in response to pattern or beat codes which do not adhere to the grammar as indicated by a return to the reset state [0]. The current count for each continuous recognition machine is compared against a defined threshold value in one or more clauses, in one or more rules.

The continuous recognition machine for recognition of sinus tachycardia and normal sinus rhythm employs the look-up table of FIG. 8, using both a strict adherence to grammar (basic behavior) and less a less strict adherence to the grammar (exponential decay), with transitions between the two types of counter behavior defined according to the rules set forth below. The continuous recognition machine for sinus tachycardia and normal sinus rhythm employs a count, "CRMedST" which is incremented, up to a maximum count, e.g. 13, in response to each transition to a non-reset state (or in response to the first R-R interval after a power-on reset or other device reset, where the pattern code is unknown). On each ventricular event, all CRM counts are updated by the processor and compared against applicable recognition threshold values. The value of CRMedST is compared to its corresponding CRM threshold value, e.g. 6, in a clause of the rule for recognizing sinus tachycardia.

If the pattern code associated with the present beat resets the continuous recognition machine of FIG. 8, and the counter behavior is presently set to "basic behavior", CRMedST is reset to 0. If the pattern code associated with the present beat resets the continuous recognition machine of FIG. 6, and the counter behavior is presently set to "exponential decay", CRMedST is decremented by the CRMedST decrement amount. If after decrementing, CRMedST is then less than 0, the counter behavior is set to "basic behavior" and CRMedST is set to 0. If after decrementing, CRMedST is greater than 0, then the CRMedST decrement amount is set to either twice the present decrement amount or to the decremented value of CRMedST, whichever is less. By this mechanism, the amount of the decrement increases a factor of two with each successive failure to meet the pattern grammar, hence an exponential decay of the value of CRMedST with successive failures to meet pattern grammar.

If the pattern code associated with the present beat does not reset the continuous recognition machine of FIG. 8 or is unknown, the value of CRMedST is incremented by 1, up to the maximum of 13. If the CRMedST counter behavior is set to "basic behavior", and the incremented value of CRMedST is greater than or equal to the associated CRM threshold value, e.g. 6, then CRMedST counter behavior is set to "exponential decay" and the CRMedST decrement amount is set to 2. If the CRMedST counter behavior is set to "exponential decay", and the incremented value of CRMedST equals the maximum count the CRMedST decrement amount is set to 2.

FIG. 9 illustrates the look-up table employed in conjunction with the continuous recognition machine for recognizing beat code sequences corresponding to normal sinus rhythm or to sinus tachycardia in the presence of far field R-wave sensing in the atrium. The rules for incrementing and decrementing the associated count CRMedSTFR correspond to those for incrementing and decrementing the value of CRMedST, as discussed above.

If the beat code associated with the present beat resets the continuous recognition machine of FIG. 9, and the counter behavior is presently set to "basic behavior", CRMedSTFR is reset to 0. If the beat code associated with the present beat resets the continuous recognition machine of FIG. 9, and the counter behavior is presently set to "exponential decay", CRMedSTFR is decremented by the CRMedSTFR decrement amount. If after decrementing, CRMedSTFR is then less than 0, the counter behavior is set to "basic behavior" and CRMedSTFR is set to 0. If after decrementing CRMedSTFR is greater than 0, then the CRMedSTFR decrement amount is set to either twice the present decrement amount or to the decremented amount of CRMedSTFR, whichever is less.

If the beat code associated with the present beat does not reset the continuous recognition machine of FIG. 9 or is unknown, the value of CRMedSTFR is incremented by 1, up to the maximum count, e.g. 13. If the CRMedSTFR counter behavior is set to "basic behavior", and the incremented value of CRMedSTFR is greater than or equal to the associated CRM threshold value, e.g. 6, then CRMedSTFR counter behavior is set to "exponential decay" and the CRMedST decrement amount is set to 2. If the CRMedSTFR counter behavior is set to "exponential decay", and the incremented value of CRMedSTFR equals the maximum count the CRMedST decrement amount is set to 2.

FIG. 10 is a look-up table employed by the CRM used to detect the likely occurrence of atrial fibrillation or flutter. The Count associated with the CRM is designated "CRMAL". The value of CRMAL is employed in a clause of a rule for recognizing atrial fibrillation or flutter. This continuous recognition machine requires strict adherence to the pattern grammar. The value of CRMAL is incremented by one up to the maximum count, e.g. 13, in response to any pattern code that does not reset the continuous recognition machine, and is reset to 0 whenever the continuous recognition machine is reset.

FIG. 11 is a look-up table employed by the CRM used to detect the likely occurrence of atrial-ventricular nodal tachycardia. The Count associated with the CRM is designated "CRMAVNRT". The value of CRMAVNRT is employed in a clause of a rule for recognizing AV nodal reentrant tachycardia. The value of CRMAVNRT is incremented by one up to the maximum count, e.g. 13, in response to any pattern code that does not reset the continuous recognition machine, and is reset to 0 whenever the continuous recognition machine is reset.

In addition to adherence to the defined grammars as set forth above, the rules of the present invention also employ rate and interval based recognition criteria presently employed by the Medtronic Model 7219 implantable pacemaker/cardioverter/defibrillator. These criteria are discussed in detail in U.S. Pat. No. 5,342,402, issued to Olson, incorporated herein by reference in its entirety. These criteria are also discussed below.

Presently available pacemaker-cardioverter-defibrillator devices, such as the Model 7219 PCD devices available from Medtronic, Inc., employ programmable fibrillation interval ranges and tachycardia detection interval ranges. In these devices, the interval range designated as indicative of fibrillation consists of intervals less than a programmable interval (VFDI) and the interval range designated as indicative of ventricular tachycardia consists of intervals less than a programmable interval (VTDI) and greater than or equal to VFDI. R-R intervals falling within these ranges are measured and counted to provide a count (VTEC) of R-R intervals falling within the ventricular tachycardia interval range and a count (VFEC) of the number intervals, out of a preceding series of a predetermined number (FEB) of intervals, which fall within the ventricular fibrillation interval range. VTEC is incremented in response to R-R intervals that are greater than or equal to VFDI but shorter than VTDI, is reset to zero in response to intervals greater than or equal to VTDI and is insensitive to intervals less than VFDI. VTEC is compared to a programmed value (VTNID) and VFEC is compared to a corresponding programmable value (VFNID). When one of the counts equals its corresponding programmable value, the device diagnoses the presence of the corresponding arrhythmia, i.e. tachycardia or fibrillation and delivers an appropriate therapy, e.g. anti-tachycardia pacing, a cardioversion pulse or a defibrillation pulse. In addition, the physician may optionally require that the measured R-R intervals meet a rapid onset criterion before VTEC can be incremented and can also optionally require that should a rate stability criterion fail to be met, VTEC will be reset to zero. If the device is further programmed to identify the occurrence of a fast ventricular tachycardia, detection of ventricular fibrillation or tachycardia according to the above method serves as a provisional detection, which may be modified, as discussed below. An exemplary set of parameters might be VFDI=320 ms, VFNID=18/24 preceding intervals, VTDI=400 ms, VTNID=16 intervals.

In addition to the tachycardia and fibrillation detection criteria (VTEC>=VTNID, VFEC>=VFNID) discussed above, detection of tachycardia or fibrillation detection may also be optionally accomplished using a combined count of all intervals indicative of tachycardia or fibrillation. This combined count (VFEC+VTEC) is compared to a combined count threshold (CNID). If VTEC+VFEC is equal or -greater than CNID, the device checks to see whether VFEC is at least a predetermined number (e.g. 6). If so, the device checks to determine how many of a number (e.g. 8) of the immediately preceding intervals are greater or equal to VFDI. If a predetermined number (e.g. 8) are greater than or equal to VFDI, tachycardia is detected, otherwise ventricular fibrillation is detected. If the device is further programmed to identify the occurrence of a fast ventricular tachycardia, detection of ventricular fibrillation or tachycardia according to the above method serves as a provisional detection, which may be modified, as discussed below.

In addition, the model 7219 PCD is provided with a method of distinguishing a fast ventricular tachycardia from either ventricular fibrillation or slow ventricular tachycardia. In conjunction with fast ventricular tachycardia detection, the physician determines whether detection of a fast ventricular tachycardia is to be accomplished following a provisional diagnosis of ventricular tachycardia, following a provisional diagnosis of ventricular fibrillation, or following either. If detection of fast ventricular tachycardia is enabled, then following provisional detection of ventricular tachycardia or fibrillation, as discussed above, the immediately preceding measured intervals are examined to determine whether the provisional detection of fibrillation or tachycardia should be confirmed or amended to indicate detection of fast ventricular tachycardia.

If fast ventricular tachycardia detection following a provisional detection of ventricular tachycardia is enabled, a value VFTDImax is defined, which is greater than or equal to VFDI. If fast ventricular tachycardia detection following a provisional detection of ventricular fibrillation is enabled, a value VFTDImin,, is defined, which is less than or equal to VFDI. If ventricular tachycardia is provisionally detected, intervals less than VFTDImax are taken as indicative of fast ventricular tachycardia. If ventricular fibrillation is provisionally detected, intervals greater than or equal to VFTDImin are taken as indicative of fast ventricular tachycardia.

If fibrillation was provisionally detected, the device may require that at least 7 or all 8 of the preceding 8 intervals fall within the fast ventricular tachycardia interval range (greater than or equal to VFTDImin) to detect fast ventricular tachycardia. Otherwise, the provisional detection of ventricular fibrillation is confirmed. If ventricular tachycardia is provisionally detected, the device may only require that at least 1 or 2 of the preceding 8 intervals fall within the fast ventricular tachycardia interval range (less than VFTDImax in order to detect fast ventricular tachycardia. Otherwise, the provisional detection of (slow) ventricular tachycardia is confirmed.

The entire arrhythmia detection methodology of the Model 7219 PCD is not retained in the disclosed embodiment of the present invention, in that the above described criteria for detecting fast ventricular tachycardia are not employed, with the criteria for detecting ventricular tachycardia and ventricular fibrillation employed as the two lowest priority rules for triggering delivery of ventricular anti-tachyarrhythmia therapies. However, the fast tachycardia recognition criteria described above could readily be added if desired, in which case, the criteria for detection of ventricular fibrillation, fast ventricular tachycardia and ventricular tachycardia according to this methodology would comprise the three lowest priority rules employed for detection of ventricular tachyarrhythmia.

The arrhythmia detection and classification scheme of the present invention also employs a measurement of R-R interval variability, as disclosed in U.S. Pat. No. 5,330,508 issued to Gunderson and incorporated herein by reference in its entirety. R-R interval variability is measured by the processor sorting the 12–18 previous measured R-R intervals into bins in RAM, each bin being 10 ms in width, spanning the range of 240 ms through 2019 ms. The sum (RR Modesum) of the numbers of intervals in the two bins individually having the highest numbers of intervals is calculated and compared against preset threshold values. The higher the value of RR Modesum, the lower the variability of RR intervals, and the more likely the rhythm is a monomorphic ventricular tachycardia. The RR Modesum is compared against various threshold values in clauses of rules for detecting ventricular tachycardia, ventricular tachycardia in the presence of supraventricular tachycardia, atrial fibrillation or flutter, and AV nodal reentrant tachycardia. A buffer of 18 measured intervals is also provided in RAM. Intervals less than 240 ms do not appear in the bins, but are loaded in the buffer. Following detection initialization or power on reset, the buffer is cleared, and thereafter intervals are entered in the buffer. If fewer than 12 intervals are in the buffer, the value of RR Modesum is defined as "unknown". If 12 or more intervals are in the buffer, RR Modesum is equal to the fraction defined by the number of intervals stored in the buffer residing in the two bins having the highest numbers of intervals divided by the number of intervals in the buffer. For example, if the RR Modesum threshold is set at 0.75, then RR Modesums of 9/12, 12/16, 14/18, etc. would meet the threshold.

In conjunction with the operation of rules intended to identify the likely occurrence of ventricular and supraventricular tachycardia, the microprocessor also keeps track of the number of R-R intervals which likely contain sensed atrial events caused by far field R-waves, out of a preceding series of R-R intervals. If an R-R interval is determined likely to contain a far field R-wave, the Far Field R-wave Criterion is met for that R-R interval. The microprocessor determines that an event sensed in the atrium is likely a far field R-wave, according to the following methodology.

The microprocessor maintains a Far RP buffer in RAM containing the eight most recent R-P intervals less than 160 ms and a Far PR buffer containing the eight most recent P-R intervals less than 60 ms. In response to the occurrence of R-R interval having a P count equal to 2, the R-P and P-R intervals for the R-R interval are compared to fixed thresholds. For example, the processor may check to determine whether the P-R interval is less than or equal to 60 milliseconds or whether the R-P interval is less than or equal to 160 milliseconds. It should be kept in mind that in conjunction with an R-R interval having a P count of 2, the R-P interval is measured between the ventricular event initiating the R-R interval and the first occurring atrial event and the P-R interval is measured between the second to occur atrial event and the ventricular event ending the R-R interval.

If the P-R interval is less than or equal to 60 milliseconds, the processor subtracts the shortest P-R interval (PRmin) in the Far PR buffer from the longest (PRmax). If the value of the difference is less than or equal to 30 milliseconds, the processor compares the P-P interval between the two atrial events during the R-R interval under consideration with the P-P interval separating the first atrial event in the R-R interval in consideration from the last atrial event in the proceeding R-R interval. If the difference between these two values is greater than or equal to 30 milliseconds, the processor subtracts the current P-R interval from the average (PRave) of the P-R intervals in the buffer. If the absolute value of the difference is less than a defined Far R Stability value, e.g. 20 ms, the R-R interval under consideration likely includes a far field R-wave and the Far Field R-Wave Criterion is met..

Similarly, if the measured R-P interval in the R-R interval under question is less than or equal to 160 milliseconds, the processor subtracts the, shortest (RPmin) of the eight R-P intervals in the Far RP buffer from the longest (RPmax) R-P interval in the buffer if the difference is less than or equal to 50 ms, the processor compares the P-P interval in the R-R interval under question with the P-P interval separating the final atrial event of the preceding R-R interval to the first atrial event of the R-R interval under question. If, as discussed above, the difference between the two PP intervals is greater than or equal to 30 milliseconds, the processor subtracts the current R-P interval from the average (RPave) of the R-P intervals in the buffer. If the absolute value of the difference is less than the Far R Stability value, the R-R interval under consideration likely includes a far field R-wave and the Far Field R-Wave Criterion is met.

The processor keeps track of the number of R-R intervals out of a preceding series of intervals (e.g., 12 intervals) which likely contain a far field R wave. This number (Far R Counter) is compared to a threshold value (Far R Threshold, e.g., 10) to determine whether it is likely that a heart rhythm which appears to have a high atrial rate is in fact the result of far field R-wave sensing.

Figure 12:
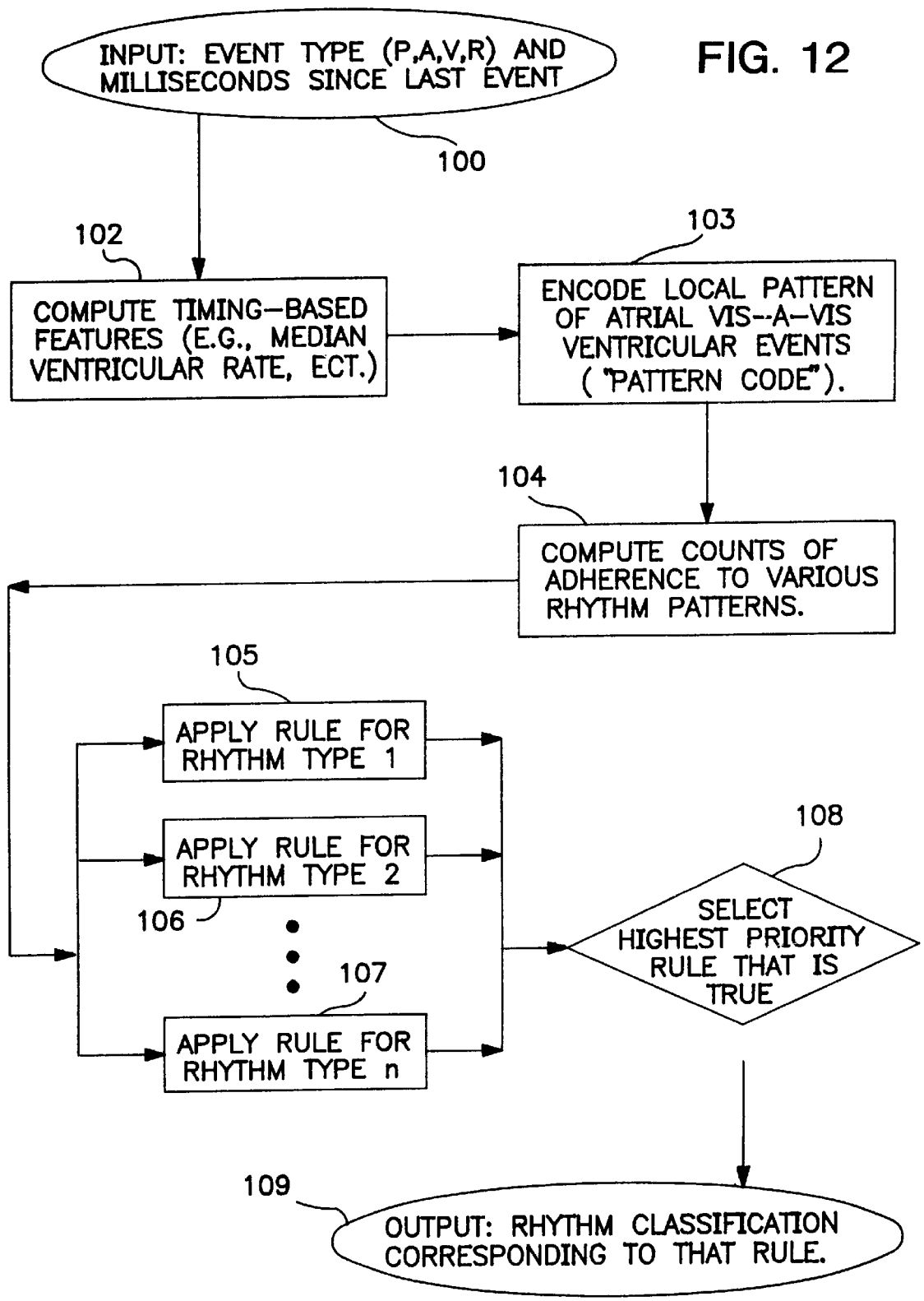
FIG. 12 is a functional flowchart illustrating the operation of the heart rhythm classification methodology employed by the present invention.

FIG. 12 illustrates the basic operation of a device according to the present invention, in response to the occurrence of atrial and ventricular events. In response to an atrial ventricular event at 100, the type of event is stored, and also a number of counts and values referred to above are updated. In particular, in response to an atrial or ventricular event, the processor stores information as to the P count, i.e. the number of atrial events received since the last ventricular event, and an R count, i.e. the count of the number of ventricular events received since the last atrial event, and R-R, R-P, P-P and P-R intervals, as appropriate. The processor maintains buffers in the RAM, in which the following information is stored: the 12 most recent P-P intervals are stored, the 12 most recent R-R intervals are stored, the 8 immediately preceding R-P intervals, the 8 most recent P-R interval values, and the times of occurrence of atrial and ventricular events over the preceding 12 R-R intervals, employed in conjunction with the detection of far field R waves, as discussed above. In addition, the processor also maintains a memory buffer of the bin indexes for the preceding 18 R-R intervals, as described above in conjunction with the computation of the RR Modesum value and a buffer containing the number of RR intervals over the preceding sequence of a programmable number of R-R intervals, which have durations less than FDI, as discussed above in conjunction with the detection criterion adapted from the Model 7219 PCD device.

At 102, the processor updates all timing based features associated with the occurrence of atrial and ventricular events, including all computations necessary to update the buffers described above, computation of all timing based values associated with the Model 7219 detection criteria described above, including updating of the value of VTEC, VFEC, the onset and stability counters, as well as updating the RR Modesum value as described above, computation of the median values of the 12 preceding stored R-R interval durations, computation of the median value of the stored preceding 12 P-P intervals and R-R intervals, as appropriate, and in the case of a ventricular event, updates the beat code for the R-R interval ending with the ventricular event.

In addition to these functions, in response to the occurrence of a ventricular event, the processor at 103 computes the corresponding pattern code, as described above, associated with the R-R interval ending with the ventricular event and at 104 updates the continuous recognition machine counters, as described above and the other diagnostic criteria described below in conjunction with the various rules. The processor now has stored in RAM all information necessary to apply the hierarchical set of rules used to identify the particular type of rhythm under way.

At 105, 106, 107, the processor determines which of the various available rules have all of their respective clauses satisfied. As discussed above, one, more than one, or no rules may have their causes all satisfied. If more than one rule is true or "fires", the rule of highest priority is selected at 108, leading to a rhythm classification corresponding to that rule at 109. In response to the classification of the rhythm, the device delivers therapy or prevents delivery of therapy, depending upon the rhythm identified. In the absence of any rules being identified, the device withholds anti-tachycardia therapy. If the device is programmed to provide bradycardia backup pacing, it continues to do so. If not, the device simply continues to monitor the rhythm of the heart, until one or more rules fire.

In the context of the specific embodiment disclosed herein, several possible rhythm classifications are provided by the rule set. These include ventricular fibrillation, ventricular tachycardia, simultaneous ventricular and supraventricular tachycardia, simultaneous ventricular fibrillation and supraventricular tachycardia, atrial fibrillation or flutter, sinus tachycardia, AV nodal re-entrant tachycardia, normal sinus rhythm or "unclassified" rhythms, when no rules are "firing".

In conjunction with the present invention, 12 separate rules are employed to identify the various rhythm types listed above. These rules are in order of priority.

1. VF+SVT Rule
2. VT+SVT Rule
3. A Flutter Rule
4. A Fibrillation Rule
5. ST Rule
6. AVNRT Rule
7. NSR Rule
8. VT* Rule
9. VF Rule - 7219
10. VT Rule - 7219
11. Sustained AF Rule
12. Sustained AT Rule Of the above rules, the A Flutter Rule, the A Fibrillation Rule, the ST Rule, the AVNRT Rule and the NSR Rule all prevent delivery of ventricular anti-tachyarrhythmia therapies. The VF+SVT rule, the VT+SVT rule, the VT* Rule, the VF Rule -7219 and the VT Rule - 7219 all trigger delivery of ventricular anti-tachyarrhythmia therapies. The Sustained AF Rule and the Sustained AT Rule trigger delivery of atrial ant-arrhythmia therapies. As such, the hierarchical structure of the rule base is such that the to five lowest priority rules are provided for triggering therapy, superseded by five intermediate priority rules for inhibiting delivery of anti-tachyarrhythmia therapy, which in turn are superseded by two high priority rules, triggering delivery of anti-tachycardia therapy. This hierarchical rule structure is believed to be unique in the context of automated devices for triggering delivery of anti-tachycardia therapies.

Figure 13:
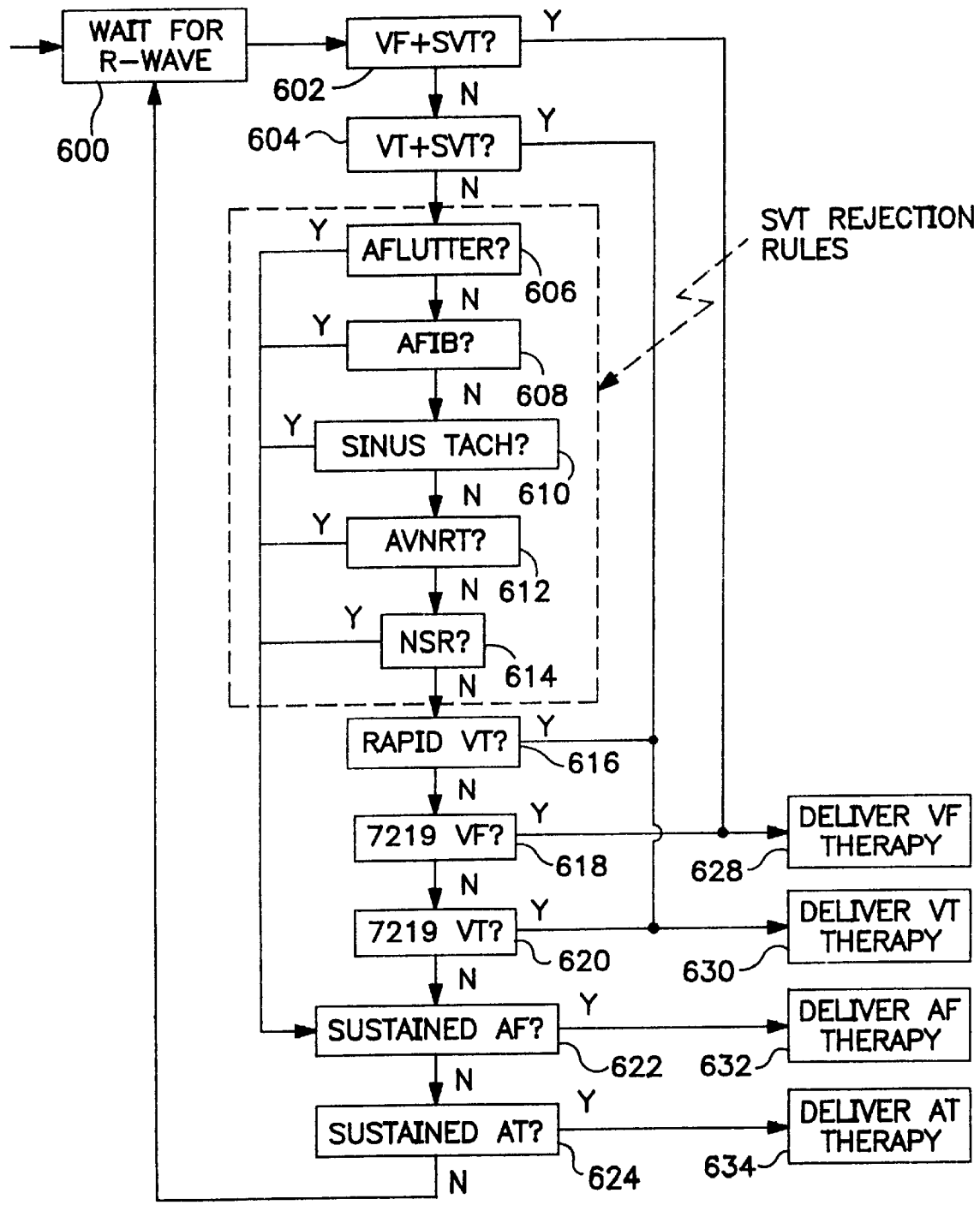
FIG. 13 is a functional flowchart illustrating the interaction of the various rules for initiation and prevention of anti-arrhythmia therapies.

FIG. 13 illustrates the prioritization of the various rules, in the form of a flowchart. In response to occurrence of an R-wave at 600, each rule is examined by the processor, in order of the priority listed above until one is met. If the first rule met is the VF+SVT Rule or VT+SVT Rule at 602 or 604, VF therapy or VT therapy is delivered at 628 or 630, and delivery of atrial anti-arrhythmia therapies is prevented. If one of the rules which prevents treatment of ventricular tachyarrhythmias is met at 606, 608, 610, 612 or 614, the processor examines whether the Sustained AF Rule or Sustained AT Rule is the first rule met at 622 and 624. If one of these rules is met, AF therapy or AT therapy is delivered at 632 or 634. If no rules preempting ventricular therapies are met the processor examines whether the rules at 616, 618 or 620 are met, and if so triggers delivery of VF or VT therapy at 628 or 630, preventing delivery of AF or AT therapy. Similarly, if no rules preventing or triggering ventricular anti-tachyarrhythmia therapy are met, the processor determines whether the Sustained AF Rule or the Sustained AT Rule is the first rule met at 622 and 624 and if so triggers delivery of the appropriate therapy at 628 or 630. The specific rules and their individual clauses are described in detail below, illustrating the interrelation of the various timing based and pattern based criteria described above.

1. VF+SVT Rule

The VF+SVT Rule is the highest priority rule employed by the device, and detects the simultaneous presence of VF and SVT. If it is met, it triggers delivery of the next scheduled ventricular fibrillation therapy, typically a high voltage defibrillation pulse. This rule has five clauses and is set true, or "fires" when all five clauses are satisfied. The first clause requires that ventricular fibrillation detection is programmed on and that any of rules 3–7 for preventing delivery of ventricular anti-tachyarrhythmia therapies has also been programmed on and that VFEC is greater or equal to VFNID, as discussed in conjunction with the VF detection criteria employed with the Model 7219 discussed above. The second clause requires that the median value for the preceding 12 R-R intervals (RR median) is less than a preset minimum cycle length. This minimum cycle length may be VTDI, if VT detection is programmed on or may be VFDI, if VT detection is programmed off, or may be an interval separately programmable by the physician, or defined as a fixed value within the device. The third clause requires that the median value for the preceding 12 R-R intervals is greater than a preset SVT Minimum Cycle Length. This SVT Minimum Cycle Length must be less than VTDI, if VT detection is programmed on and must be greater than VFDI, if VT detection is programmed off and may be an interval separately programmable by the physician in conjunction with programming of VTDI or VFDI.

The fourth clause employs an AF* Evidence Counter Criterion which supports or refutes the presence of atrial fibrillation using an up-down counting algorithm performed by the processor, which increments or decrements an AF* Evidence Counter based on atrial and ventricular pattern information. The AF* Evidence Counter Criterion will be met when the AF* Evidence Counter is greater than or equal to a predefined AF* Score Threshold, e.g. 6. Once the AF/AT Evidence Counter Criterion is met, it will remain satisfied as long as the AF* Evidence Counter is greater than or equal to a predefined AF* Score Hysteresis Threshold, e.g. 5. The fourth clause continues to be met as long as the AF* Counter Criterion continues to be met.

The AF* Evidence Counter is incremented and decremented as follows. If the number of atrial events or P count in the current R-R interval is 1 and the current beat code is the same as the previous beat code, the AF* Evidence Counter is decremented by 1, down to a minimum of 0. If the number of atrial events is 1 but if the beat codes are different the AF* Evidence Counter remains unchanged. If the number of atrial events in the current R-R interval is greater than 2, then the AF* Evidence Counter is incremented by 1, up to an AF* Score Maximum value, e.g. 10. If the number of atrial events in the current R-R interval is 2 and the current beat code and the previous beat code are the same and the Far Field R-Wave criterion discussed above is met for the preceding RR interval, the AF* Evidence count remains unchanged. Otherwise the AF* Evidence Counter is incremented by 1, up to the AF* Maximum Score value.

The fifth and final clause of the rule employs an AV Dissociation Count Criterion implemented by the processor, which defines an AV Dissociation Count, which is the number of a preceding series of R-R intervals, e.g. 8 R-R intervals, which meet an AV Dissociation Criterion. The AV Dissociation Criterion is met if there are no paced or sensed atrial events in the current R-R interval or the absolute value of the difference between the current P-R interval and the average of the previous 8 P-R intervals is greater than 40 ms. The AV Dissociation Count Criterion is met when the AV Dissociation Count is greater than or equal to a defined AV Dissociation Count Threshold, e.g. 4. When the A V Dissociation Count Criterion is met, the fifth clause is satisfied.

If all of these clauses are satisfied, the rule is set true and "fires" triggering delivery of the next scheduled ventricular fibrillation therapy. Firing of the VF+SVT rule supersedes firing of any other rules 2. VT+SVT Rule The second highest priority rule is intended to identify the simultaneous occurrence of ventricular tachycardia and supraventricular tachycardia. This rule contains six clauses, all of which must be satisfied in order for the rule to be set true or "fire". The first clause requires that ventricular tachycardia detection be enabled, and that the value of VTEC be greater than or equal to VTNID (as discussed above in conjunction with the Model 7219 detection criteria). The second clause requires that the AF* Evidence Counter Criterion as discussed above is met. The third clause requires that the AV Dissociation Count Criterion discussed above is met. The fourth clause requires that the RR median is less than VTDI. The fifth clause requires that the RR median is greater than the SVT Minimum Cycle Length discussed above. The sixth and final clause requires that the RR Modesum as described above is either unknown or greater than a defined VT Plus RR Modesum Threshold, e.g. 0.75 of the preceding 12–18 R-R intervals.

If all of these clauses are satisfied, the rule is set true and "fires" triggering delivery of the next scheduled ventricular tachycardia therapy. Firing of the VT+SVT rule supersedes firing of any other rules, with the exception of the VF+SVT rule, described above.

SVT Rejection Rules.

The SVT rejection rules 3–7 cannot be applied if unless VT detection is Programmed on, there have been at least enough intervals since initialization of detection to fill the RR buffer, e.g. 12, and the RR median is greater than the SVT Minimum Cycle Length. The rules also have the following sets of additional clauses.

3. A Flutter Rule

Due to the importance of distinguishing rapid ventricular rhythms due to atrial fibrillation or flutter from tachycardias of ventricular origin, two separate rules are provided for identifying the likely occurrence of atrial fibrillation or flutter (or other atrial tachycardia). The first of these two rules has two clauses which must be satisfied in order for the rule to be met. The first clause requires that the value of CRMAL is greater than or equal to its corresponding recognition threshold, e.g. 6. The second clause requires that the Far Field R-Wave Count Criterion is met. The Far Field R-Wave Count Criterion is met when the Far Field R-Wave Count is less than a defined Far Field R-Wave Count Threshold, e.g. 10 of the preceding 12 R-R intervals. If both clauses are met, the rule is set true or "fires". If this is the highest priority firing rule, delivery of ventricular anti-tachyarrhythmia therapy is prevented even if lower priority ventricular tachycardia or ventricular fibrillation rules are met while the rule is firing.

The A Flutter Rule is a "sticky" rule, meaning that when met, it remains met unless its clauses remain unsatisfied over a sequence of RR intervals. The processor accomplishes this result by setting an associated AF Rejection Sticky Count to a predefined value, e.g. 6 whenever the rule is met. For each R-R interval for which either the first or second clause is not met, the Sticky Count is decremented by 1 to a minimum of 0. The rule continues to fire as long as the Sticky Count remains above 0.

4. A Fibrillation Rule

The second rule directed toward detection of the occurrence of atrial fibrillation or flutter (or other atrial tachycardia) has four clauses which must be met. The first clause requires that the Far Field R-Wave Count Criterion, discussed above, is met. The second clause requires that the median value of the P-P interval, over the preceding 12 R-R intervals be known, and that it be less than a preset value, e.g. 87.5% of the corresponding RR median value, over the preceding 12 intervals. The third clause requires that AF* Evidence Counter Criterion is satisfied, as discussed above. The fourth clause requires that the RR Modesum is less than or equal to a defined AF Modesum Threshold, e.g. 0.5 of the previous 12–18 intervals. If all four clauses of the rule are satisfied, the rule is set true or "fires". If this rule is the highest firing priority rule, delivery of ventricular anti-tachyarrhythmia therapies is prevented.

The A Fibrillation Rejection Rule is a "sticky" rule, meaning that when met, it remains met unless its clauses remain unsatisfied over a sequence of RR intervals. The processor accomplishes this result by setting an associated AFib Rejection Sticky Count to a predefined value, e.g. 6 whenever the rule is met. For each R-R interval for which any of the four clauses are not met, the Sticky Count is decremented by 1 to a minimum of 0. The rule continues to fire as long as the Sticky Count remains above 0. The Sticky Count is reset to 0 on initialization of detection and whenever a higher priority SVT rejection rule is satisfied.

5. ST Rule

This rule is directed toward recognition of sinus tachycardia, and includes three clauses, of which either the first clause or the second and third clauses must be met in order for the rule to fire. The clause requires that CRMedST exceed its corresponding recognition threshold, e.g.,. 6. If this clause is satisfied, the rule fires. The second clause requires that the Far Field Counter Criterion discussed above be met. The third clause requires that the CRMedSTFR exceed its corresponding recognition threshold, e.g. 6. If the second and third clauses are satisfied, the rule fires. If the ST Rule is the highest priority rule firing, delivery of anti-tachycardia therapies is prevented.

The ST rule is a "sticky" rule, meaning that when met, it remains met unless its clauses remain unsatisfied over a sequence of RR intervals. The processor accomplishes this result by setting an associated Sinus Rejection Sticky Count to a predefined value, e.g. 6 whenever the rule is met. For each R-R interval for which either the first clause is not met or for which one or both of the second and third clauses is not met, the Sticky Count is decremented by 1 to a minimum of 0. The rule continues to fire as long as the Sticky Count remains above 0. The Sticky Count is reset to 0 on initialization of detection and whenever a higher priority SVT rejection rule is satisfied.

6. AVNRT Rule

This rule is directed toward detection of AV nodal re-entrant tachycardia. The rule includes two clauses, each of which must be satisfied in order for the rule to fire. The first clause requires that CRMAVNRT exceed its corresponding threshold value, e.g. 6. The second clause requires that RR Modesum is greater than or equal to a defined AVNRT Modesum Threshold, e.g. 0.25 of the preceding 12–18 R-R intervals. If both clauses are satisfied, the rule is set true or "fires". If it is the highest priority firing rule, it prevents delivery of ventricular anti-tachycardia therapies.

The AVNRT Rule is a "sticky" rule, meaning that when met, it remains met unless its clauses remain unsatisfied over a sequence of RR intervals. The processor accomplishes this result by setting an associated AVNRT Sticky Count to a predefined value, e.g. 6 whenever the rule is met. For each R-R interval for which either the first or second clause is not met, the Sticky Count is decremented by 1 to a minimum of 0. The rule continues to fire as long as the Sticky Count remains above 0. The Sticky Count is reset to 0 on initialization of detection and whenever a higher priority SVT rejection rule is satisfied.

7. NSR Rule

This rule is directed toward detection of a normal sinus rhythm, and includes three clauses of which either the first clause or the second and third clauses must be met in order for the rule to fire. The clause requires that CRMedST exceed its corresponding recognition threshold, e.g.,. 6. If this clause is satisfied, the rule fires. The second clause requires that the Far Field Counter Criterion discussed above be met. The third clause requires that the CRMedSTFR exceed its corresponding recognition threshold, e.g. 6. If the second and third clauses are satisfied, the rule fires. If the ST Rule is the highest priority rule firing, delivery of anti-tachycardia therapies is prevented.

The ST rule is a "sticky" rule, meaning that when met, it remains met unless its clauses remain unsatisfied over a sequence of RR intervals. The processor accomplishes this result by setting an associated Sinus Rejection Sticky Count to a predefined value, e.g. 6 whenever the rule is met. For each R-R interval for which either the first clause is not met or for which one or both of the second and third clauses is not met, the Sticky Count is decremented by 1 to a minimum of 0. The rule continues to fire as long as the Sticky Count remains above 0. The Sticky Count is reset to 0 on initialization of detection and whenever a higher priority SVT rejection rule is satisfied.

The next three rules are ventricular fibrillation and tachycardia detection rules which trigger delivery of ventricular anti-tachyarrhythmia therapies.

8. VT* Rule

The VT* Rule discriminates fast VT with regular cycle lengths from VF. This rule has three clauses which must be satisfied, in order for the rule to be set true. The first clause simply requires that VF detection and VT detection are enabled and that the model 7219 VF detection criteria are met, i.e. VFEC is greater than or equal to VFNID. The second clause requires that RR median is greater than or equal to the Fast VT Minimum Cycle length, discussed above. The third clause requires that the VT* RR Modesum Criterion is satisfied. The VT* RR Modesum Criterion is satisfied when RR Modesum is either unknown or greater than or equal to the a defined Fast VT Modesum Threshold, e.g. 0.75 of the preceding 12–18 R-R intervals.

9. VF Rule - 7219

This rule corresponds to the detection criteria for ventricular fibrillation as set forth above in conjunction with the description of the Model 7219 device. If VF is detected using these criteria, the rule is set true and "fires" if it is the highest firing rule, it triggers delivery of the next scheduled ventricular fibrillation therapy.

10. VT Rule - 7219

This rule simply restates all the ventricular tachycardia detection criteria provided in the Model 7219 device, as discussed above, with detection of fast ventricular tachycardia disabled.. In the event that this rule is the highest firing rule, it triggers delivery of the next scheduled VT therapy.

In conjunction with above rule set, it should be understood that in the event that a rule triggering delivery of a ventricular tachycardia therapy fires, subsequent firing of a rule indicative of the occurrence of a supraventricular tachycardia cannot occur, as the pattern grammar, and/or other timing criteria cannot possibly be met after initiation of anti-tachycardia therapy. However, it is certainly possible for a rule indicating the occurrence of a ventricular tachyarrhythmia to fire while a rule indicative of the occurrence of a supraventricular tachycardia is firing. In such case, the highest priority firing rule dominates. It should also be understood that rules 1–8 above are "sticky" rules, meaning that once a rule has fired, it will continue to fire until one or more clauses of the rule are not satisfied for a sequence of a predetermined number of R-R intervals. A nominal value for this predetermined number of R-R intervals is three, however, it is envisioned that the parameter may be programmable by the physician. This feature is intended to prevent a temporary violation of one of the clauses of a rule, for one or two beats, to override the firing of the rule. This is particularly important in the context of the rules intended to detect the likely occurrence of atrial tachycardias, where a one or two beat failure of the rule to be met could well result in the delivery of a ventricular anti-tachycardia therapy, in conjunction with the firing of a lower priority VT or VF detection rule, resulting in inappropriate delivery of ventricular anti-tachycardia therapy.

11 and 12. Sustained AF and Sustained AT rules.

In conjunction with a preferred embodiment of the invention, rules for triggering delivery of anti-arrhythmia therapies in response to detected sustained atrial fibrillation and/or sustained atrial tachycardia are also included. These rules are interrelated in operation and so are discussed together. Both rules cannot be met simultaneously. In conjunction with these rules, an additional set of defined parameters is employed. The additional parameters include an atrial fibrillation detection interval (AFDI), which may be for example 150–300 ms, an atrial tachycardia detection interval (ATDI), which may be, for example, up to 450 ms, but in any case greater than AFDI, and a minimum atrial tachycardia interval (AT Minimum Interval), which may be for example 100–300 ms, but in any case less than ATDI. These parameters, and others, are used by the processor in conjunction with an additional set of diagnostic criteria, as set forth below.

A first criterion, associated with detection of atrial fibrillation is the AF Rate Zone Criterion. This criterion in turn is based upon two measured characteristics of the heart rhythm, including the median interval separating preceding atrial depolarizations (PP Median) and the regularity of the atrial cycle length (Cycle Length Regularity Counter Criterion). On each ventricular event, the buffer containing the previous 12 atrial cycle lengths will be examined to determine the median P-P interval and to determine regularity. The atrial cycle lengths are classified as being regular on a given ventricular event if the difference between the second to longest and the second to shortest atrial cycle length in the buffer is less than or equal to the PP Median divided by 4. The Atrial Cycle Length Regularity criterion will be satisfied if the atrial cycle length regularity condition is met on 6 of the most recent 8 ventricular events. The AF Rate Zone Criterion is satisfied when the PP Median is less than the programmed AFDI if Sustained AT detection is programmed off. If Sustained AT detection is programmed on then the AT Rate zone Criterion is met when the PP Median is less than the programmed AFDI, and either the PP Median is less than the programmed AT Minimum Interval or the Cycle Length Regularity Counter Criterion is not satisfied.

A second criterion, associated with detection of atrial tachycardia is the AT Rate Zone Criterion. The AT Rate Zone criterion uses the PP Median and the Atrial Cycle Length Regularity Criterion to identify AT and to discriminate it from AF. The AT Rate Zone Criterion is satisfied when the PP Median is less than the programmed ATDI and greater than or equal to the programmed AFDI, or when the PP Median is less than AFDI but greater than or equal to the programmed AT Minimum Interval and the Atrial Cycle Length Regularity Counter Criterion is satisfied.

A third criterion, associated with detection of both AF and AT is the AF/AT Evidence Counter Criterion which supports or refutes the presence of an atrial arrhythmia using an up-down counting algorithm which increments or decrements an AF/AT Evidence Count based on atrial and ventricular pattern information. The AF/AT Evidence Counter Criterion will be met when the AF/AT Evidence count is greater than or equal to a predefined AF/AT Score Threshold, e.g. 32 Once the AF/AT Evidence Counter criterion is met, it will remain satisfied as long as the AF/AF Evidence count is greater than or equal to a predefined AF/AT Score Hysteresis Threshold, e.g. 27.

In conjunction with the AF/AT evidence Counter Criterion, several additional characteristics of the heart's rhythm are monitored. One additional monitored characteristic is the Sinus Rhythm Counter Criterion, which identifies regular sinus rhythm with 1:1 conduction or a paced rhythm. The Sinus Rhythm Counter (SR Counter) is be affected by the beat code as defined above, as follows. If the beat code is 0, 1 is added to the SR Counter up to a maximum of 255. Otherwise the SR Counter is set to 0. The Sinus Rhythm Counter Criterion will be satisfied when the SR Counter is greater than or equal to a predefined the AF Reset Count Threshold, e.g. 5. The Sinus Rhythm Counter Criterion is suspended while a therapy operation is in progress. The SR Counter is set to zero when detection is initialized.

Also employed in conjunction with the AT/AF Evidence counter is the Sinus Rhythm with Far Field R-wave Criterion, which identifies sinus rhythm in the presence of far field R-waves. On each ventricular event a Sinus Rhythm with Far Field R-wave Counter will be updated as follows. If the Far Field R-wave criterion discussed above is satisfied for the current RR interval and the current ventricular beat code is 9, 4 or 6, 1 is added to the Sinus Rhythm with Far Field R-wave Counter up to a maximum of 255. Otherwise the Sinus Rhythm with Far Field R-wave Counter is reset to 0. The Sinus Rhythm with Far Field R-wave Counter Criterion is satisfied when the Sinus Rhythm with Far Field R-wave counter is greater than or equal to the AF Reset Count Threshold. The Sinus Rhythm with Far Field R-wave Counter Criterion is suspended while a therapy operation is in progress. The Sinus Rhythm with Far Field R-wave Counter is initialized to 0 when detection is initialized.

On each ventricular event the AF/AT Evidence Counter will be updated as follows. If the Sinus Rhythm Count Criterion is satisfied or the Sinus Rhythm with Far Field R-wave Count Criterion specified is satisfied, the AF/AT Evidence Counter is reset to 0.

If neither the Sinus Rhythm Count Criterion is satisfied or the Sinus Rhythm with Far Field R-wave Count Criterion is satisfied, and if the P count (number of atrial events in the RR interval, discussed above in conjunction with Beat Codes) is less than or equal to 1 and the AF/AT Evidence Counter was incremented on the last ventricular event, 1 is added to the AF/AT Evidence Counter up to a predefined the AF Score Maximum Value, e.g. 47.

If neither the Sinus Rhythm Count Criterion is satisfied or the Sinus Rhythm with Far Field R-wave Count Criterion is satisfied, and the P count is equal to 2 and the Far Field R-wave Criterion discussed above is met for the current ventricular event and the AF/AT Evidence Counter was incremented on the last ventricular event, 1 is added to the AF/AT Evidence Counter up to a predefined the AF Score Maximum Value.

If neither the Sinus Rhythm Count Criterion is satisfied or the Sinus Rhythm with Far Field R-wave Count Criterion specified is satisfied, and the P count is equal to 2 and the Far Field R-wave criterion discussed above is not met for the current ventricular event, 1 is added to the AF/AT Evidence Counter up to the AF Score Maximum Value.

If neither the Sinus Rhythm Count Criterion is satisfied or the Sinus Rhythm with Far Field R-wave Count Criterion specified is satisfied, and the P count is more than 2, 1 is added to the AF/AT Evidence Counter up to the AF Score Maximum Value.

If none of the above conditions applies, 1 is subtracted from the AF/AT Evidence Counter down to a minimum value of 0.

Detection of sustained atrial fibrillation or sustained atrial tachycardia begins with preliminary detection of these rhythms. Preliminary detection of AF occurs when the AF/AT Detection Evidence Count Criterion and the AF Rate Zone Criterion discussed above are both met. Preliminary detection of AF will result in the start of the sustained AF/AT duration timer, described in more detail below. Preliminary detection of AT occurs when the AF/AT Detection Evidence Count Criterion and the AT Rate Zone Criterion discussed above are both met. Preliminary detection of AT similarly results in the start of the sustained AF/AT duration timer. Preliminary Detection of AT or AF will be possible only if VT or VF is not detected by the device using the rules described above. AT and AF detection will be suspended if a detected VT or VF episode is in progress.

The sustained AF/AT duration timer is initiated on preliminary detection of AF or AT and continues to time until termination of atrial tachyarrhythmia is detected. The sustained duration timer continues to time through delivery of anti-atrial tachyarrhythmia therapies. The sustained AF/AT duration timer is used in conjunction with one or more defined minimum required durations, e.g. 1–1440 minutes, programmable by the physician, associated with either the arrhythmia determined to be underway and/or the type of therapy next scheduled for delivery. for example, the minimum sustained duration for a scheduled pacing pulse level therapy would typically be less than for a high voltage therapy delivered in response to detection of AF. No therapy for a detected arrhythmia, i.e. AT or AF can be delivered following delivery of a therapy for the same arrhythmia which has a longer defined minimum sustained duration. The type of arrhythmia underway, following activation of the sustained AF/AT duration timer may be AT, AF, or undefined, is determined according to the following method. The criteria for preliminary detection of AF and AT discussed above are continually applied following initial detection. The criterion (AF or AT) presently met is the arrhythmia determined to be present. A failure to meet the AF/AT Evidence Counter Criterion or a failure to meet either of the AT and AF Rate Zone Criteria results in the arrhythmia being designated as unclassified. If the arrhythmia is classified as AT or AF, and if the applicable minimum required duration associated with the arrhythmia determined to be present and/or the next scheduled therapy has been exceeded, the next scheduled therapy is delivered, to any associated additional preconditions for therapy discussed below also being met. No therapy can be delivered while the arrhythmia is unclassified.

Figure 14:
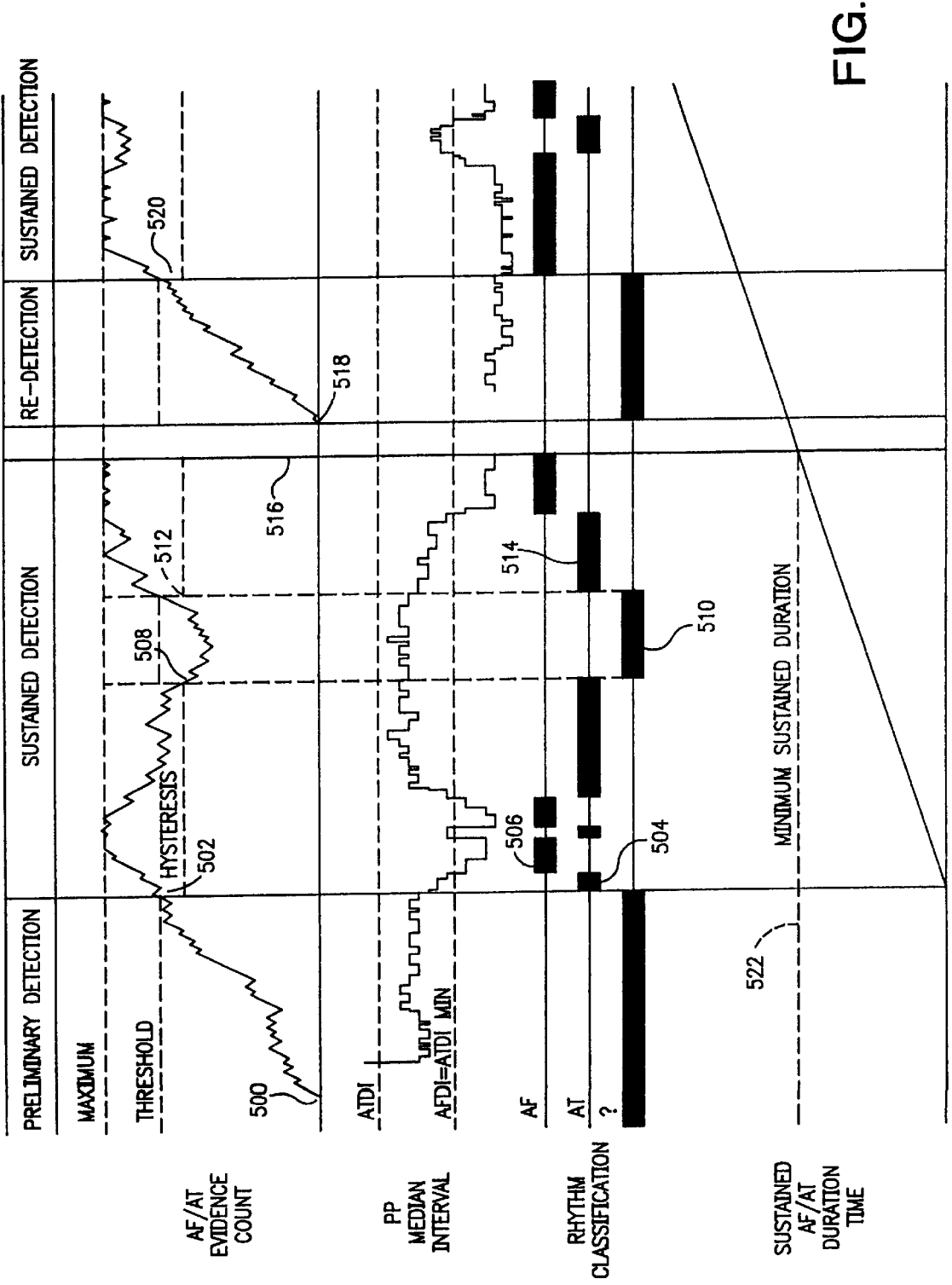
FIG. 14 is a diagram illustrating the operation of the atrial fibrillation/atrial tachycardia evidence counter.

FIG. 14 illustrates the interrelation of the sustained AF/AT duration timer, the AF/AT evidence counter and the AF and AT Rate Zone Criteria in detecting sustained AF or AT and triggering delivery of anti-atrial arrhythmia therapy. At 500, The AF/AT Evidence counter begins to be incremented as described above. Concurrently the PP Median, AF Rate Zone Criteria and AT rate Zone Criteria are monitored. Preliminary detection of AT occurs, when the AF/AT Evidence Count reaches the required minimum duration at 502, with initial classification of the arrhythmia as AT occurring at 504, as the AT Rate Zone Criterion is also concurrently met. At 506, The arrhythmia is reclassified to AF, due to the AF Rate Zone Criterion being met. Subsequent changes in classification occur, with the arrhythmia being unclassified at 510 in response to the AF/AT Evidence Counter Criterion failing to be met at 508. When the AF/AT Evidence Counter Criterion is again met at 512, the arrhythmia is classified as AT due to the AT Rate Zone criterion being met. As illustrated, a Hysteresis AF/AT Evidence count Threshold is also defined.

In FIG. 14, a single defined minimum sustained duration is illustrated at 522. This would be the case if the minimum sustained duration is defined only by the next scheduled therapy type (e.g. high voltage shock vs. low energy, pacing pulse level therapies. However, if desired, different minimum sustained durations may also be defined for different arrhythmia types, as discussed above. At 516, the applicable minimum sustained duration is reached, concurrent with the arrhythmia being classified as AF, triggering delivery of the next scheduled AF therapy. Following delivery of the therapy, the AF/AT Evidence Counter is reset at 518, with redetection of AF occurring at 520, when the AF Evidence Counter again reaches the threshold.

As discussed above, the Sustained AF/AT Duration Timer continues to time until termination of atrial tachyarrhythmia is detected. Satisfaction of the AF/AT Episode Termination criterion will defines the end of a sustained AF/AT Episode, resets the Sustained AF/AT Duration Timer, and restores preliminary AF/AT detection conditions. The AF/AT Episode Termination Criterion is satisfied when either the Sinus Rhythm Counter Criterion discussed above is satisfied, or the Sinus Rhythm With Far Field R-wave Counter Criterion discussed above is satisfied, or detection has resumed for a predetermined time period, e.g. three minutes after being suspended (as discussed below) and the arrhythmia has not been classified in that time period as AF or AT, or a VT episode or VF episode is detected as discussed above.

All AF/AT detection is temporarily suspended when an atrial anti-tachyarrhythmia therapy is in progress. When detection is suspended the device will operate as follows. The arrhythmia classification will be set to unclassified, but the device will continue to update the Sustained AF/AT Duration Timer, if it is currently in operation. Similarly, the device will continue to look for AF/AT termination of awhile the device is in the suspend detection state. When suspension of detection ends the device will initialize detection criteria other than the Sustained AF/AT Duration Timer, such that a full detection (or re-detection) sequence will be required to classify the rhythm or detect episode termination. Temporary suspension of detection will end when delivery of therapy is terminated.

Optionally, the device may be programmable to also suspend AF/AT detection for 16 ventricular intervals following therapy delivery. During this period the effective AFDI and ATDI will be set to zero (i.e. the AF and AT detection zones will be disabled). This feature is believed particularly desirable in conjunction with the High frequency stimulation therapies disclosed in the Mehra and Duffin patents cited above, to provide additional time needed for termination of atrial tachyarrhythmias treated with such therapy.

In preferred embodiments of the invention, additional prerequisite criteria for delivery of anti-atrial tachyarrhythmia therapies may be included. For example, AF/AT therapy may be disabled due to ventricular arrhythmia detection following AF/AT Therapy. Confirmation of AF/AT and/ or expiration of a minimum delay since the delivery of a previous therapy may be prerequisites and a specified time of day may be prerequisites to delivery of AF/AT therapy. Expiration of a maximum sustained AF/AT duration and/or a predefined number of therapies having been delivered in a preceding time period may prevent delivery of AT/AF therapy. These additional criteria are discussed below.

The detection of VT or VF following the delivery of an AF/AT therapy prior to-either re-detection of AF/AT or AF/AT episode termination can optionally cause the device to disable all subsequent AF/AT therapy until the condition has been cleared by the physician. An AF/AT therapy disabled flag in this case would be set by the microprocessor would be available and may be cleared via telemetry, by the physician, if desired. This feature will prevent further AT/AF therapy when it has been closely associated with a detected episode of VT or VF. AF/AT detection may continue following termination of the VT or VF episode, however, no AF/AT therapies would be delivered.

Optionally, the device may retain a running count of the number high voltage AF/AT therapies delivered over the preceding 24 hours. An Atrial High Voltage Therapies per 24 Hour Cycle Criterion would be satisfied if the atrial high voltage therapy count is less than a programmed Maximum Number of Atrial High Voltage Therapies per 24 Hour Cycle. Satisfaction of the Atrial High Voltage Therapies per 24 Hour Cycle Criterion may be required as prerequisite to delivery of high voltage AT/AF therapies.

As discussed in U.S. patent application Ser. No. 08/434, 899, by Bardy, for an "Atrial Defibrillator and Method of Use", filed May 3, 1995 and incorporated herein by reference in its entirety, it may also be desirable to limit delivery of high voltage therapies to a defined time period when the patient is likely to be asleep. A Time of Day Atrial High Voltage Therapy Criterion can prevent automatic atrial defibrillation therapy from being delivered outside of a programmed time window.

If a sustained episode of AF or AT persists for long enough, the physician may wish to prevent further attempts of the device to terminate the arrhythmia. In such case, A Time to Stop Therapy Criterion may be employed to disable AF and AT therapy when the Sustained AF/AT Duration Timer exceeds a programmed Time to Stop Therapy, e.g. more than 48 hours.

Confirmation of that a sinus rhythm has not resumed may also be required as a prerequisite to delivery of AF/AT therapy. An AF/AT Therapy Confirmation Criterion will prevent the initiation of atrial therapy when sinus rhythm has returned but AF/AT episode termination has not yet been detected. The AF/AT Therapy Confirmation Criterion may be satisfied for the current ventricular interval if either the number of atrial events in the current ventricular interval is greater than two, or the number of atrial events in the current ventricular interval is two and the atrial interval for both events is either less than the ATDI if AT detection is ON or AFDI if AT detection is OFF.

A minimum interval between delivered therapies may also be a prerequisite to AF therapy. A Post Therapy AF Therapy Delay Criterion may be employed to delay the initiation of AF therapy delivery of a prior AF therapy. This will allow nonsustained atrial fibrillation resulting from the therapy to spontaneously terminate before AF therapy intervention. It may also be used to create a delay between AF therapies. The Post AF Therapy Delay may be, for example, 240 seconds. The Post Therapy AF Therapy Delay Criterion is satisfied if either no AF therapies have been delivered in the current AF/AT episode, or he number of seconds since the last therapy scan delivered with the post therapy AF therapy delay enabled is greater than the Post Therapy AF Therapy Delay, and satisfaction of this criterion may be a prerequisite to delivery of AF therapy.

In conjunction with commercial embodiments of devices according to the present invention, it is anticipated that selecting which of the various available rules are to be activated in the device may prove an overwhelming task for the physician. As such, it is proposed that VF, VT, AF and AT detection and treatment using rules 8, 9, 10, 11 and 12 may be programmed only in specific combinations, such that if AF, AT or VT detection and therapies are enabled, then VF detection and therapies must also be enabled as a safeguard. Similarly, if AT detection and therapies are enabled, then AF and VF detection and therapies must also be enabled.

With regard to rules 3–7, these rules may be programmed on or off individually by the physician. However, simultaneous VF and SVT detection and therapy using rule 1 are automatically enabled in response to any of rules 3–7 being enabled along with VF detection and therapy using rule 9. Similarly, simultaneous VT and SVT detection and therapy using rule 2 is automatically enabled in response to any of rules 3–7 being enabled along with VT detection and therapy using rule 8 or 10. It should also be noted that under this proposed approach to selecting sets of rules to be activated, that the highest priority rules 1 and 2, which trigger delivery of therapy are not enabled in the absence of ennoblement of one or more of intermediate priority rules 3–7, which inhibit delivery of anti-tachycardia therapy. The reason for this is that the higher priority rules 1–2 set forth stricter requirements for detection of ventricular fibrillation and tachycardia than rules 8–10, and are thus unnecessary, in the absence of intermediate priority rules 3–7, capable of overriding the VT and VF detection criteria defined by these rules.

While the above rule set is described in terms of initial detection of a tachyarrhythmia, such a prioritized rule system may also be employed in conjunction with redetection of a tachyarrhythmia or in detection of a change of type of ventricular tachyarrhythmia. However, due to the complexities of such a system, it is proposed that as a practical matter, the device may simply be programmed such that following delivery of an initial tachycardia therapy, detection of termination of the arrhythmia and redetection of ventricular tachyarrhythmias be conformed to that employed in the Model 7219, for the sake of ease of use and simplicity. In such an embodiment, delivery of an initial ventricular anti-tachyarrhythmia therapy will result in disablement of Rules 1–8 until subsequent detection of termination of the detected ventricular tachyarrhythmia, following which Rules 1–8, as selected by the physician, may be reactivated. Redetection of atrial tachyarrhythmias is done using the criteria for preliminary detection, as described above in conjunction with rules 11 and 12.

While the AF/AT Evidence counter, the AF and AT Rate Zones and the AF/AT Sustained Duration Timer are disclosed as useful in detecting atrial tachyarrhythmias, it should be understood that the basic framework for arrhythmia detection they provide may also be useful to detect ventricular tachyarrhythmias. In particular, the basic functional interrelation of these elements of the device may be applicable in an analogous fashion to distinguish between ventricular tachycardias and/or nodal tachycardias.

2. Operation of Patient Activator

Figure 15:
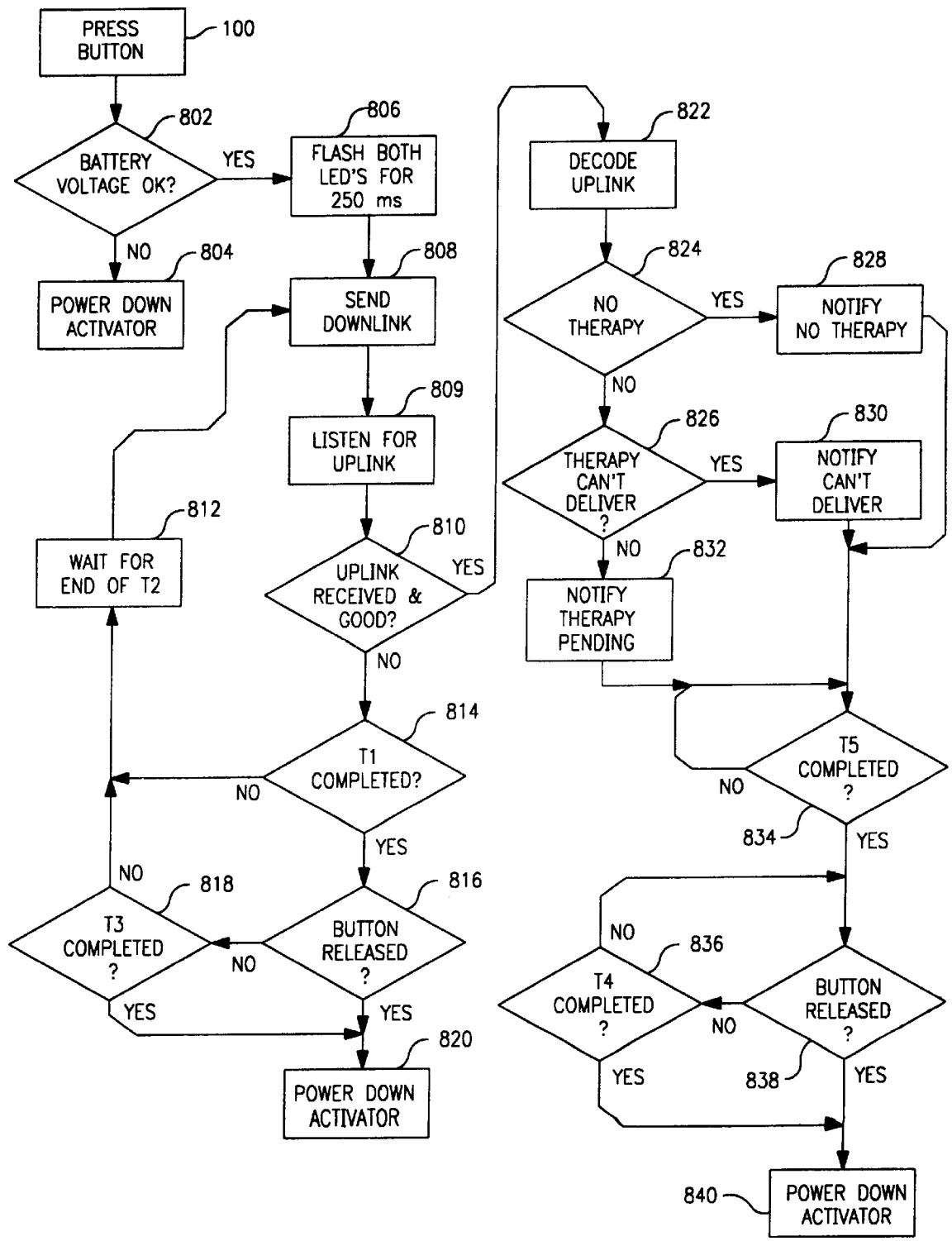
FIG. 15 is a functional flowchart illustrating the operation of the patient activator.

FIG. 15 is a functional flow chart illustrating the operation of the patient activator in conjunction with a request for therapy. In response to the pressing of the activator button at 800, the power/switching/battery monitoring circuit 120 powers up the activator, and the microprocessor defines two time intervals thereafter, including interval T-1, which may be 10 seconds, and interval T-3, which may be 60 seconds. The microprocessor polls the battery monitoring circuit 120 at 802 to determine whether adequate battery voltage is present, if not, the microprocessor provides a signal to circuitry 120 at 804 to shut down the activator. If battery voltage is adequate, the microprocessor triggers the LED drivers 114 to flash both the green and amber LEDs for 250 milliseconds, which indicates that the activator is operative. At 808, the microprocessor modulates a programming data stream, which is presented to antenna driver/switching circuit 124, for transmission to the implanted device. The microprocessor then waits at 809 for a return uplink signal from the implanted device, indicating that the patient activation request has been received. On transmission of the downlink, the microprocessor also defines a time interval T-2, which for example, may be 250 milliseconds. At 810, the microprocessor determines whether it has received a valid uplink from the implanted device. If the downlink to the device was received, the corresponding uplink would start within T-2 minus the duration of the uplink (e.g. 70 ms.) following the end of transmission of the downlink. If an uplink is not received or the uplink that is received cannot be adequately decoded, the device checks at 814 to determine whether T-1 has terminated. If not, the device waits until the end of time interval T-2 at 812, and repeats the downlink transmission, until either time period T-1 has been completed, or a good uplink has been received.

If time period T-1 expires prior to receiving a good uplink from the implanted device, the microprocessor checks at 816 to see if the push button is currently being pressed, indicating that the patient still desires delivery of therapy. If not, the microprocessor signals the power/switching/monitoring circuit 120 to power down the device. If the button has not been released after expiration of time interval T-1, the microprocessor checks at 818 to determine whether time interval T-3 has expired, which is taken as an indication that communication with the implanted device simply is not possible, and the microprocessor simply shuts down the activator at 820. If the button is being pressed, and time interval T-3 has not been completed, the activator continues to send downlink patient therapy requests every 250 milliseconds, until either the button is released, or T-3 expires.

On receipt of a valid uplink at 810, the microprocessor defines two additional time periods including T-4, which may be 60 seconds since the uplink was received, and T-5, which may be 10 seconds since the uplink was received. At 822 the uplink is decoded, and the activator is notified whether or not the patient's heart rhythm indicates that therapy is appropriate at 824. If therapy is not appropriate, at 828 the microprocessor triggers the speaker driver 110 to deliver an audible signal, for example, a sequence of three rising tones, and activates the LED driver circuitry 114 to flash the green indicator light on the case of the activator, indicating to the patient that therapy is not warranted and will not be delivered. If therapy is appropriate but cannot presently be delivered at 826, the microprocessor notifies the patient at 830 by activating the speaker driver 110 to produce a different audio signal, for example, a falling two-tone sequence. In addition, the microprocessor activates the LED driver circuitry 114 to cause both the amber and the green lights to flash. In this case, the patient knows that the therapy is warranted but will not be delivered. If, on the other hand, the implanted device determines that the requirements for the therapy are presently met, the microprocessor notifies the patient at 832 by a third, distinguishable audio signal, for example a steady, pulsing tone, in conjunction with activation of the amber LED by LED driver circuitry 114. The particular audio and visual signals provided to the patient, are of course, arbitrary, and any set of similar warning signals which allows the patient to reliably distinguish between the three states, i.e., no therapy, therapy presently unavailable, and therapy pending, are believed to be workable in the context of the present invention. On expiration of interval T-5, the LED and audio signals are terminated, and the microprocessor checks at 838 to determine whether the push button is released. On either expiration of time interval T-4 at 836 or release of the push button at 838, the activator is powered down.

3. Arrhythmia Detection Following Patient Request

Operation of the implantable device in response to a patient-activation request is as follows. The request for patient-activated therapy is received by telemetry receiver 330 by means of antenna 332. The decoded telemetry signal is applied to multiplexer 220, and provided to the microprocessor by means of address/data bus 218. The microprocessor in response to receiving a request for patient-activated therapy, attempts to determine whether patient-activated therapy is appropriate, in accordance with a subset of the arrhythmia detection criteria described in detail above. In the particular embodiment disclosed herein, the microprocessor determines whether a detected AF/AT episode is in progress. As discussed above in conjunction with FIG. 14, an episode is considered to be in progress if the AF/AT evidence count previously reached its threshold value and termination has not been detected.. In addition, the microprocessor checks to determine whether the AF/AT Therapy Confirmation criterion described above is satisfied and checks to determine that the Time to Stop Therapy criterion described above is not satisfied and that AF/AT therapy has not been disabled due to detection of ventricular tachyarrhythmia following delivery of an atrial therapy, also as described above. The microprocessor also checks to determine whether patient activated therapy has been enabled by programming and if the patient activated therapy is a high voltage therapy such as cardioversion or defibrillation the processor checks to see whether the high voltage charging circuit has been disabled for example due to excessive charging times as in currently marketed implantable defibrillators. If the rhythm classification is either AF or AT, AF/AT therapy has not been disabled, the AF/AT Therapy Confirmation criterion is satisfied and the Time to Stop Therapy criterion is not satisfied, patient activated therapy is enabled and the charging circuit is not disabled, the patient-activated therapy is scheduled and the microprocessor triggers an uplink transmission to the patient activator indicating that therapy is pending. If the programmed patient initiated therapy is atrial defibrillation or cardioversion, an additional prerequisite to scheduling the therapy is that either at least two of the preceding twelve ventricular intervals are greater than the ventricular refractory interval (indicating that synchronization is likely possible) or there have been fewer than twelve intervals since the detection functions were last initialized.

Once the therapy is scheduled, it will be delivered at such time as the rhythm classification is either AT or AF, as discussed in conjunction with FIG. 14, provided that the AF/AT Confirmation criterion remains satisfied and the Time to Stop Therapy criterion remains unsatisfied, and provided that the pending therapy is not canceled, as discussed below. It should be noted that the criteria for scheduling the therapy as pending do not require the rhythm to be classified as AF or AT, so it is possible to schedule a therapy without meeting the criteria for delivering it. When the patients rhythm thereafter meets the criteria for delivery, the therapy is initiated.

A pending therapy may be canceled before delivery if the need for therapy terminates or the device becomes incapable of delivering the therapy. For example, therapy may be canceled if termination of the AF/AT episode is detected, if AF/AT therapy is disabled due to detection of ventricular tachyarrhythmia following a previous atrial anti-arrhythmia therapy, or if the Time to Stop Therapy criterion is met. If the scheduled therapy is defibrillation or cardioversion, the therapy may also be canceled upon a determination that the time to charge the high voltage output capacitors exceeds a preset duration, as is conventional in commercially marketed implantable defibrillators. Finally, therapy may be canceled if the criteria for delivery of the therapy are not satisfied within a predefined time period, e.g. one minute, following scheduling of the therapy. By this mechanism, failure of the rhythm to continuously meet the criteria for delivery will be tolerated for a period of time, but not indefinitely.

The methodology employed by the implanted device and patient activator in combination thus provides a mechanism for delivering patient requested therapy even if, the implanted device is unable to classify the rhythm at the time the button on the activator is pushed, so long as the criteria for delivery are met within a reasonable time thereafter. The criteria for triggering a patient activated therapy are based upon the criteria for triggering a device initiated therapy, but are less stringent, as they are a subset of the required criteria for device initiated therapy. The criteria for delivery are thus likely to be met quickly if therapy is appropriate, facilitating the prompt, appropriate delivery of therapy in response to a patients request.

The above disclosure sets forth a device in which sensed events in the atrium and ventricle are used to control delivery of electrical therapy to treat tachyarrhythmias. However, the basic methodology of the present invention is believed equally applicable to devices which deliver other types of therapies, such as automatic delivery of antarrhythmic drugs, as disclosed in U.S. Pat. No. 4,146,029, issued to Ellinwood, U.S. Pat. No. 5,527,344, issued to Arzbaecher et al., and U.S. Pat. No. 5,087,243, issued to Avitall, all of which are incorporated herein by reference in their entireties. Identification of the origin of the arrhythmia and delivery or withholding of therapy in response to a patient request would be equally valuable in such devices. Furthermore, while it seems likely that commercial embodiments of devices according to the present invention will require the use of a microprocessor in order to perform the calculations and analysis steps required for arrhythmia detection, it is within the realm of possibility that some or all of the detection and control functions provided by the microprocessor might instead be provided by means of a full custom, integrated circuit, particularly a circuit in which a state counter is employed instead of stored software, in order to control sequential operation of the digital circuitry, along the general lines of the circuits disclosed in U.S. Pat. No. 5,088,488, issued to Markowitz et al. and U.S. Pat. No. 5,052,388, issued to Sivula et al., both of which are incorporated herein by reference in their entireties.

The above disclosed embodiment employs a particular detection methodology which is unique to the products of the assignee. However, it is believed that the basic mechanism of the present invention could also be beneficially incorporated into anti-arrhythmia devices using different detection methods, such as disclosed in any of the various patents cited above directed to implantable anti-arrhythmia devices, by employing a subset of the criteria or less stringent individual criteria required for device initiated therapy as a confirmation of a patient. For example, in a device which relies on parameters such as rate, sustained high rate, rate regularity, and/or sudden onset as in presently marketed implantable defibrillators, fewer of these parameters could be employed for patient-triggered therapy than for device initiated therapies. Alternatively, or in addition, the individual criteria may be altered, for example by a lowered required rate or a shortened sustained high rate period, as may be appropriate. In addition, the provision of a time interval following patient activation during which the criteria for therapy delivery must be met is believed valuable even in the context of patient activators which require verification of arrhythmia using the same criteria as for device initiated therapy. Thus, the above description should be considered exemplary, rather than limiting, with regard to the interpretation of the following claims.

In conjunction with the above disclosure, we claim:

1. An arrhythmia treatment system, comprising an implantable anti-arrhythmia device and an external activator;

the implantable device comprising:
  means for defining a first set of arrhythmia detection criteria:
  means for monitoring a patients heart rhythm;
  means for determining whether the patient's heart rhythm meets the first set of criteria;
  means in responsive to a determination that the patient's heart rhythm meets the first set of criteria; for delivering a first anti-arrhythmia therapy
  means for defining a second set of arrhythmia detection criteria;
  means for receiving a patient activation signal;
  means responsive to receipt of a patient activation signal for determining whether the patient's heart rhythm meets the second set of criteria;
  means responsive to a determination that the patient's heart rhythm meets the second set of criteria, for delivering a second anti-arrhythmia therapy; and
  means for transmitting information to the external activator indicative of whether the second therapy is to be delivered in response to the patient activation signal;

the external activator comprising:
  a patient operable control;
  signal generator means responsive to the patient operable control for transmitting the patient activation signal to the implanted device; and
  receiver means for receiving information transmitted from said implantable device indicative of whether the second therapy is to be delivered in response to the patient activation signal; and
  indicator means responsive to said receiver means for indicating to the patient whether the second therapy is to be delivered.

2. A system according to claim 1, wherein the implanted device further comprises means for transmitting information to the external receiver indicative of whether delivery of the second therapy is appropriate.

3. A system according to claim 1 or claim 2 wherein the indicator means comprises means for generating a first patient perceptible signal if the second therapy is to be delivered.

4. A system according to claim 3 wherein the indicator means comprises means for generating a second patient perceptible signal, different from the first patient perceptible signal, if the second therapy is not to be delivered.

5. A system according to claim 1 or claim 2 wherein the indicator means comprises means for generating a first patient perceptible signal if the second therapy is not to be delivered and the second therapy is not appropriate.

6. A system according to claim 5 wherein the indicator means comprises means for generating a second patient perceptible signal different from the first patient perceptible signal if the therapy is appropriate and the second therapy is to be delivered.

7. A system according to claim 6 wherein the indicator means comprises means for generating a third patient perceptible signal different from the first and second patient perceptible signals if the second therapy is appropriate and is not to be delivered.

8. A system according to claim 1 or claim 2 wherein the indicator means comprises means for generating audible signals.

9. A system according to claim 1 or claim 2 wherein the indicator means comprises means for generating visible signals.

10. A system according to claim 1 or claim 2 wherein the indicator means comprises means for generating audible and visible signals.

11. An arrhythmia treatment system, comprising an implantable anti-arrhythmia device and an external activator;

the implantable device comprising:
means for defining a set of arrhythmia detection criteria:
means for monitoring a patients heart rhythm;
means for determining whether the patient's heart rhythm meets the set of criteria;
means for receiving a patient activation signal;
means responsive to receipt of a patient activation signal for determining whether the patient's heart rhythm meets the set of criteria;
means responsive to a determination that the patient's heart rhythm meets the set of criteria, for delivering an anti-arrhythmia therapy; and
means for transmitting information to the external activator indicative of whether the therapy is to be delivered in response to the patient activation signal and indicative of whether delivery of the therapy is appropriate, the external activator comprising:
a patient operable control;
signal generator means responsive to the patient operable control for transmitting the patient activation signal to the implanted device; and
receiver means for receiving information transmitted from the implantable device indicative of whether the therapy is to be delivered in response to the patient activation signal and indicative of whether delivery of the therapy is appropriate; and
indicator means responsive to the receiver means for indicating to the patient whether the therapy is to be delivered and whether delivery of the therapy is appropriate.

12. A system according to claim 11 wherein the indicator means comprises means for generating a first patient perceptible signal if the therapy is not to be delivered and the therapy is not appropriate.

13. A system according to claim 12 wherein said indicator means comprises means for generating a second patient perceptible signal different from said first patient perceptible signal if the therapy is appropriate and the therapy is to be delivered.

14. A system according to claim 13 wherein the indicator means comprises means for generating a third patient perceptible signal different from the first and second patient perceptible signals if the therapy is appropriate and is not to be delivered.

15. A system according to claim 11 wherein the indicator means comprises means for generating audible signals.

16. A system according to claim 11 wherein the indicator means comprises means for generating visible signals.

17. A system according to claim 11 wherein the indicator means comprises means for generating audible and visible signals.

18. An arrhythmia treatment system, comprising an implantable anti-arrhythmia device and an external activator;

the implantable device comprising:
means for defining a set of arrhythmia detection criteria:
means for monitoring a patients heart rhythm;
means for receiving a patient activation signal;
means responsive to receipt of a patient activation signal for determining whether the patient's heart rhythm meets the set of criteria; and
means for transmitting information to the external activator indicative of whether the patient's heart rhythm meets the set of criteria;

the external activator comprising:
a patient operable control;
signal generator means responsive to the patient operable control for transmitting the patient activation signal to the implanted device; and
receiver means for receiving information transmitted from the implantable device indicative of whether the patient's heart rhythm meets the set of criteria; and
indicator means responsive to the receiver means for indicating to the patient whether the patient's heart rhythm meets the set of criteria.

19. A system according to claim 18 wherein the indicator means comprises means for generating a first patient perceptible signal if the patient's heart rhythm meets the set of criteria.

20. A system according to claim 19 wherein the indicator means comprises means for generating a second patient perceptible signal different from the first patient perceptible signal if the patient's heart rhythm does not meet the set of criteria.

21. A system according to claim 18 wherein the indicator means comprises means for generating audible signals.

22. A system according to claim 18 wherein the indicator means comprises means for generating visible signals.

23. A system according to claim 18 wherein the indicator means comprises means for generating audible and visible signals.

* * * * *